US011202779B2

(12) United States Patent
Vilenchik et al.

(10) Patent No.: US 11,202,779 B2
(45) Date of Patent: *Dec. 21, 2021

(54) COMBINATIONS FOR THE TREATMENT OF NEOPLASMS USING QUIESCENT CELL TARGETING WITH EGFR INHIBITORS

(71) Applicant: Felicitex Therapeutics, Inc., Natick, MA (US)

(72) Inventors: Maria Vilenchik, Newton, MA (US); Michael Frid, Medford, MA (US); Alexandra Kuznetsova, Natick, MA (US); Yuriy Gankin, Newton, MA (US); Marc Duey, Chester Springs, PA (US)

(73) Assignee: Felicitex Therapeutics, Inc., Newton, MA (US)

( * ) Notice: Subject to any disclaimer, the term of this patent is extended or adjusted under 35 U.S.C. 154(b) by 126 days.

This patent is subject to a terminal disclaimer.

(21) Appl. No.: 16/442,973

(22) Filed: Jun. 17, 2019

(65) Prior Publication Data

US 2019/0298723 A1    Oct. 3, 2019

Related U.S. Application Data

(62) Division of application No. 15/488,116, filed on Apr. 14, 2017, now Pat. No. 10,322,128.

(60) Provisional application No. 62/323,537, filed on Apr. 15, 2016.

(51) Int. Cl.
| | | |
|---|---|---|
| *A61K 31/519* | (2006.01) | |
| *A61K 31/506* | (2006.01) | |
| *A61K 31/517* | (2006.01) | |
| *A61K 45/06* | (2006.01) | |

(52) U.S. Cl.
CPC .......... *A61K 31/519* (2013.01); *A61K 31/506* (2013.01); *A61K 31/517* (2013.01); *A61K 45/06* (2013.01)

(58) Field of Classification Search
CPC .. A61K 31/519; A61K 31/506; A61K 31/517; A61K 45/06
USPC ...................................................... 514/252.2
See application file for complete search history.

(56) References Cited

U.S. PATENT DOCUMENTS

| | | |
|---|---|---|
| 10,314,843 B2 | 6/2019 | Vilenchik et al. |
| 10,322,128 B2 | 6/2019 | Vilenchik et al. |
| 2014/0275064 A1 | 9/2014 | Leblond et al. |
| 2014/0371251 A1 | 12/2014 | Aberger et al. |
| 2015/0266825 A1 | 9/2015 | Hood et al. |
| 2015/0292032 A1 | 10/2015 | Vilenchik et al. |
| 2017/0296541 A1 | 10/2017 | Vilenchik et al. |
| 2017/0296542 A1 | 10/2017 | Vilenchik et al. |

FOREIGN PATENT DOCUMENTS

| | | |
|---|---|---|
| WO | 2016/055916 A1 | 4/2016 |
| WO | 2017014788 A1 | 1/2017 |

OTHER PUBLICATIONS

U.S. Appl. No. 15/488,116, filed Apr. 14, 2017, Combinations for the Treatment of Neoplasma Using Quiescent Cell Targeting With EGFR Inhibitors.
U.S. Appl. No. 15/488,143, filed Apr. 14, 2017, Combinations for the Treatment of Neoplasms Using Quiescent Cell Targeting and Inhibitors of Mitosis.
U.S. Appl. No. 16/436,305, filed Jun. 10, 2019, Combinations for the Treatment of Neoplasms Using Quiescent Cell Targeting and Inhibitotrs of Mitosis.
Anderson el al. "The Dual Pathway Inhibitor Rigosertib Is Effective in Direct Patient Tumor Xenografts of Head and Neck Squamous Cell Carcinomas" Molecular Cancer Therapeutics. Jul. 19, 2013 (Jul. 19, 2013) vol. 12, p. 1994-2005.
Chaffer, C. L. et al., "A perspective on cancer cell metastasis," Science. Mar. 25, 2011;331(6024):1559-64. doi: 10.1126/science. 1203543.
Coller et al., A new description of cellular quiescence, PLoS Biology, 2006, v. 4, e83.
Graybill et al. "Vintafolide: a novel targeted agent for epithelial ovarian cancer," Future Oncology, Mar. 2014, vol. 10, p. 541-548 (Only Abstract Provided ).
International Search Report and Written Opinion for Application No. PCT/US2017/027719, dated Jul. 21, 2017 (13 pages).
International Search Report and Written Opinion for Application No. PCT/US2017/027734, dated Jul. 21, 2017 (10 pages).
Jackson, R. C., "The problem of the quiescent cancer cell," Adv Enzyme Regul. 1989;29:27-46.
Karikios et al. "Irreversible EGFR inhibitors in advanced non-small-cell lung carcinoma: rationale and clinical evidence" Clinical Investigation. 2012, vol. 2, p. 317-325.
Lin et al. "Metabolism and Pharmacokinetics of Allitinib in Cancer Patients: The Roles of Cytochrome P450s and Epoxide Hydrolase in its Biotransformation," Drug Metabolism & Disposition, May 2014, v 42, pp. 872-884.
Tyson et al. "Fractional proliferation: a method to deconvolve cell population dynamics from single-cell data," Nature Methods. Aug. 12, 2012 (Aug. 12, 2012) vol. 9, p. 923-928.
[No Author Listed] American cancer society "What is targeted cancer therapy?" Jun. 6, 2016; https://www.cancer.org/treatment/treatments-and-side-effects/treatment-types/targeted-therapy/what-is. html (Year: 2016) (2 pages).
Ewton et al., Mol. Cancer Ther., 2011,10(11 ), 2104-2114.
Friedman, E., Journal of Cellular Biochemistry 2007, 102 274-279.
Ciardiello et al. "the role of EGFR inhibitors in nonsmall cell lung cancer", Current Opinion in Oncology, Jan. 1, 2004, pp. 130-135.

(Continued)

*Primary Examiner* — Yevgeny Valenrod
(74) *Attorney, Agent, or Firm* — IP Supra, PLLC; Constantine Linnik

(57) ABSTRACT

The present invention provides compositions and methods for the treatment of neoplasms, in particular, by targeting of quiescent cancer cells with therapeutic agents in combination with other treatments effective against certain neoplastic conditions, in particular, anti-cancer treatment with EGFR inhibitor agents.

9 Claims, 26 Drawing Sheets

(56) References Cited

OTHER PUBLICATIONS

Extended European Search Report for Application No. 17783286.2, dated Nov. 18, 2019 (9 pages).
Regales et al. "Dual targeting of EGFR can overcome a major drug resistance mutation in mouse models of EGFR mutant lung cancer", Journal of Clinical Investigation, B M J Group, GB, vol. 119, No. 10, Oct. 1, 2009, pp. 3000-3010.

COMBINATIONS FOR THE TREATMENT OF NEOPLASMS USING QUIESCENT CELL TARGETING WITH EGFR INHIBITORS

CROSS REFERENCE TO RELATED APPLICATIONS

This application is a divisional of U.S. patent application Ser. No. 15/488,116, filed Apr. 14, 2017, which itself claims the benefit of U.S. Provisional Patent Application No. 62/323,537, filed Apr. 15, 2016, each of which is incorporated by reference herein in its entirety.

BACKGROUND

Cancer cell quiescence, effectively a cell in a state of sleep, has been recognized recently as a major mechanism of the resistance of cancer cells to treatments and for providing a pathway for disease recurrence. This quiescence, alternatively called cellular dormancy, is due to arrest at $G_0$ phase of the cell cycle. Typically, a cell enters a cell cycle from gap phase 1 ($G_1$), as shown in FIG. 1. After a synthesis phase (S) and a short pre-mitotic interval ($G_2$), the cell divides by mitosis (M) followed by a return to $G_1$. Instead of $G_1$, however, a cell can enter cellular dormancy or quiescence, designated as the $G_0$ phase. Cancer cells can either enter an irreversible state before undergoing terminal differentiation, termed senescence, or enter a reversible, true quiescent $G_0$ state from which they could resume cycling, like quiescent fibroblasts (Coller H A, Sang L, and Roberts J M (2006) A new description of cellular quiescence, *PLoS Biology* 4, e83).

A population of cells naturally may be in a quiescent state at any given time and remain quiescent for an indeterminate period until receipt of a signal to enter the cell division cycle. In one example, the proportion of cancer cells in quiescent state within a population in a tumor may be increased by environmental factors, such as lack of nutrients, hypoxia, high concentration of reactive oxygen species, etc. Cells may also be induced into the quiescent state by the action of a drug substance, as in pharmacological quiescence.

The energy and nutrient requirements of a quiescent cell are reduced relative to a dividing cell. Since current cancer therapies target dividing cells, as illustrated in FIG. 2, and therefore a cancer cell must be in the cell division cycle for such treatments to affect it. Accordingly, a quiescent cancer cell is resistant to treatments that affect one of more cellular proliferation processes by means of damaging exposed DNA, interfering with DNA replication or repair, interfering with mitosis, or other mechanisms.

Both anticancer therapeutics and radiation treatments produce adverse effects. Consequently, doses and duration of treatment are limited by toxicity and lower effective doses and/or shorter treatment durations are highly desirable. Upon reduction in doses or discontinuation of treatment, however, the surviving quiescent cancer cells can cause cancer recurrence upon re-entry to the cell cycle, the timing of which cannot be predicted. Further, metastatic cancer cells in the bloodstream may experience a period of quiescence while they adapt to their new microenvironment (Chaffer C L and Weinberg R A (2011) A perspective on cancer cell metastasis, *Science* 331, 1559-1564). Quiescent cancer cells degrade their polyribosomes, thus blocking translation and reducing total RNA and protein content. These shrunk cancer cells may be able to enter the bores of capillaries (approximately 8 µm diameter) whereas cycling cancer cells are usually much larger (20-30 µm).

Accordingly, the existence of a population of quiescent cancer cells within a neoplasm is recognized as an obstacle to successful and durable treatment (Jackson R C (1989) The problem of the quiescent cancer cell, *Advances in Enzyme Regulation* 29, 27-46). Evidence for resistance of quiescent cancer cells derived from various cancer types and to various anti-cancer treatments has been reported.

Yet, despite a growing appreciation of the importance of cancer cell quiescence, this issue remains unaddressed clinically.

SUMMARY OF THE INVENTION

The present invention provides compositions and methods for the treatment of neoplasms, in particular, by targeting of quiescent cancer cells with therapeutic agents in combination with other treatments effective against certain neoplastic conditions, in particular, anti-cancer treatment with EGFR inhibitor agents.

Generally, the invention features a method of treating a neoplasm comprising: administering to a subject in need thereof a therapeutically effective amount of (a) a therapeutic agent effective against quiescent cancer cells; and (b) second agent which is an EGFR inhibitor, wherein the two agents can be administered sequentially or concomitantly. In some embodiments, the neoplasm is a cancer or a population of cancer cells in vitro or in vivo. In some embodiments, the subject receiving the treatment is diagnosed with cancer (e.g., metastatic or pre-metastatic). In some embodiments, the subject has been previously treated with a first-line therapy against cancer. In some embodiments, the subject is treated, or has been treated, with two or more EGFR inhibitors sequentially or concomitantly.

In some embodiments, the combined treatment may result in improved outcomes, such as increased survival, reduction of severity, delay or elimination of recurrence, or reduced side effects of the primary treatments (i.e., the EGFR inhibitor). In some embodiments, the second agent is administered at a lower dose and/or for a shorter duration when administered as part of the combination as compared to a treatment with the agent alone. For example, in some embodiments, the $EC_{50}$ value of the EGFR inhibitor is at least 20% lower in the combination treatment when compared to the same treatment with EGFR inhibitor as single agent, as determined, for example, in cell-based assays. In some embodiments, the combination treatment increases fraction of apoptotic cells in a treated population as compared to either agent alone, by at least by 2-fold as determined, for example, by fraction of sub-$G_0$ phase cells in a FACS assay.

In one embodiment, the therapeutic agent effective against quiescent cancer cells is a DYRK1 inhibitor. In some embodiments, the DYRK1 inhibitor is a compound that inhibits activity of a DYRK1 kinase, either DYRK1A or DYRK1B (in vitro or in vivo), for example, with an $IC_{50}$ of 100 nM or lower in biochemical assays. In some embodiments, the DYRK1 inhibitor reduces the fraction of quiescent cancer cells (in vitro or in vivo) that would otherwise be found in the absence of such inhibitor, for example, by at least 10%. In some embodiments, the DYRK1 inhibitor inhibits both DYRK1A and DYRK1B. In some embodiments, the DYRK1 inhibitor is selective for DYRK1A or DYRK1B.

In one embodiment, the therapeutic agent effective against quiescent cancer cells is a DYRK1 inhibitor. In one embodiment, the DYRK1 inhibitor is a compound of formula I:

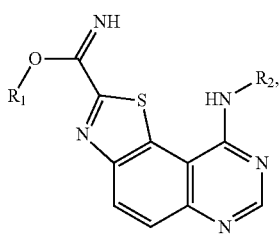

(I)

or a pharmaceutically acceptable salt or solvate thereof, wherein, $R_1$ is a substituted or unsubstituted $C_{1-8}$ alkyl, a substituted or unsubstituted phenyl, or a substituted or unsubstituted benzyl;

$R_2$ is phenyl, optionally substituted with up to four groups independently selected from halo, CN, $NO_2$, $NHC(O)C_{1-4}$ alkyl, $C_{1-4}$ alkyl, OH, $OC_{1-4}$ alkyl, wherein two adjacent groups and their intervening carbon atoms may form a 5- to 6-membered ring containing one or more heteroatoms selected from N, O, or S.

In one embodiment, the compound of formula I is selected from:

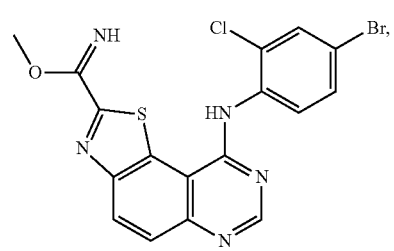

(I-1)

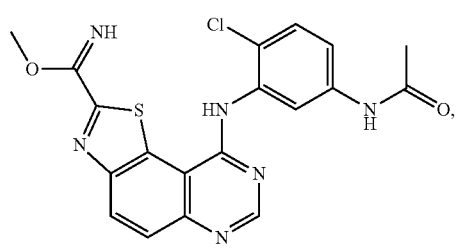

(I-2)

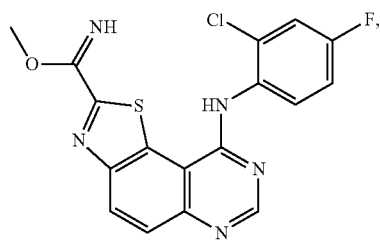

(I-3)

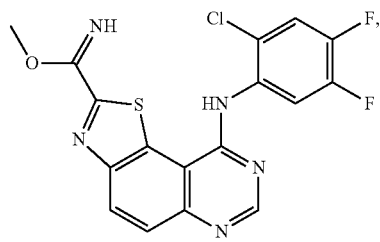

(I-4)

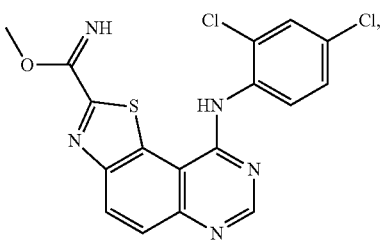

(I-5)

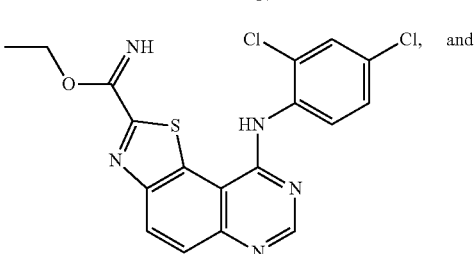

(I-6)

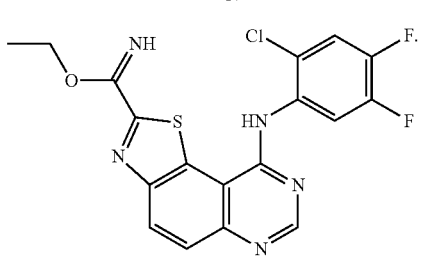

(I-7)

In another embodiment, the methods of the invention further provide (c) administering to the subject another cancer therapy, for example, radiation therapy or other cancer treatment.

In one embodiment, the methods of the invention comprise: administering to a subject in need thereof a therapeutically effective amount of (a) a therapeutic agent of formula I; (b) an EGFR inhibitor; and (c) radiation therapy; each therapy being administered sequentially or concomitantly. For example, in some embodiments, the subject is first treated with radiation therapy, whereupon the subject is administered a therapeutic agent of Formula I, alone or in combination with the EGFR inhibitor. In some embodiments, the subject is co-administered (a) the therapeutic agent effective against quiescent cancer cells, (b) the EGFR inhibitor and optionally (c) the radiation therapy. In some embodiments, the EGFR inhibitor is a compound that inhibits activity of wild type or a mutant or a truncated EGFR tyrosine kinase (in vitro or in vivo), for example, with the $IC_{50}$ of 100 nM or lower in biochemical assays. In some embodiments, the EGFR inhibitor is an EGFR inhibitor effective to treat or prevent a neoplasm, including but not limited to, all such compounds approved for the treatment of cancer and compounds that otherwise demonstrate efficacy in treating cancer in mammalian subject (e.g., mice, rats, dogs, monkeys, humans), and compounds that demonstrate efficacy against neoplastic cells in vitro. Many such compounds are known.

The EGFR inhibitor can be, for example, a small molecule or an anti-EGFR antibody.

In one embodiment, the EGFR inhibitor is a reversible EGFR tyrosine kinase inhibitor (EGFR TKI). In a further embodiment, the reversible EGFR TKI is, for example, brigatinib, CUDC-101, erlotinib, gefitinib, icotinib, lapatinib, sapitinib, vandetanib, varlitinib, tesevatinib, and Tyrphostin AG 1478. In yet another embodiment, the reversible EGFR TKI is AZD3759 or MTKi-327 (JNJ-26483327). In some embodiments, the reversible inhibitor of EGFR TKI is not erlotinib or lapatinib.

In another embodiment, the EGFR inhibitor is an irreversible EGFR TKI. In a further embodiment, the irreversible EGFR inhibitor is, for example, afatinib, olmutinib (HM61713), canertinib, CL-387785 (EKI-785), CNX-2006, dacomitinib, naquotinib (ASP8273), neratinib, osimertinib, PD168393, pelitinib, poziotinib, rociletinib, TAK285, and WZ4002. In yet another embodiment, the irreversible EGFR TKI is, for example, allitinib (ALS-1306; AST-1306), AV-412 (W-412), nazartinib (EGF816), and pyrotinib.

In yet another embodiment, the EGFR inhibitor is an antibody against EGFR, for example, cetuximab (Erbitux®) and panitumumab (Vectibix®).

In another embodiment, the neoplasm being treated is a cancer, for example, biliary cancer, brain cancer, breast cancer, cervical cancer, colon cancer, gastric cancer, kidney cancer, head and neck cancer, leukemia, liver cancer, lung cancer, lymphoma, ovarian cancer, pancreatic cancer, prostate cancer, rectal cancer, sarcoma, skin cancer, testicular cancer, thyroid cancer, or uterine cancer. In a further embodiment, the cancer is non-small cell lung cancer. In further embodiments, the cancer is primary or metastatic. In yet further embodiments, the cancer is of the type represented by the cell line types shown in the Examples. In some embodiments, the subject having cancer possesses a mutation in the EGFR gene associated with an increased risk of cancer and/or resistance to certain EGFR TKIs.

The embodiments described here are illustrative and are not meant to be limiting with regard to additional combination components, routes and order of administration, patient type (previously untreated or previously treated, absence or presence of co-morbid conditions, age, etc.), or stage of patient's disease, type of EGFR inhibitor, etc.

DETAILED DESCRIPTION OF THE INVENTION

Glossary

Figure 1:
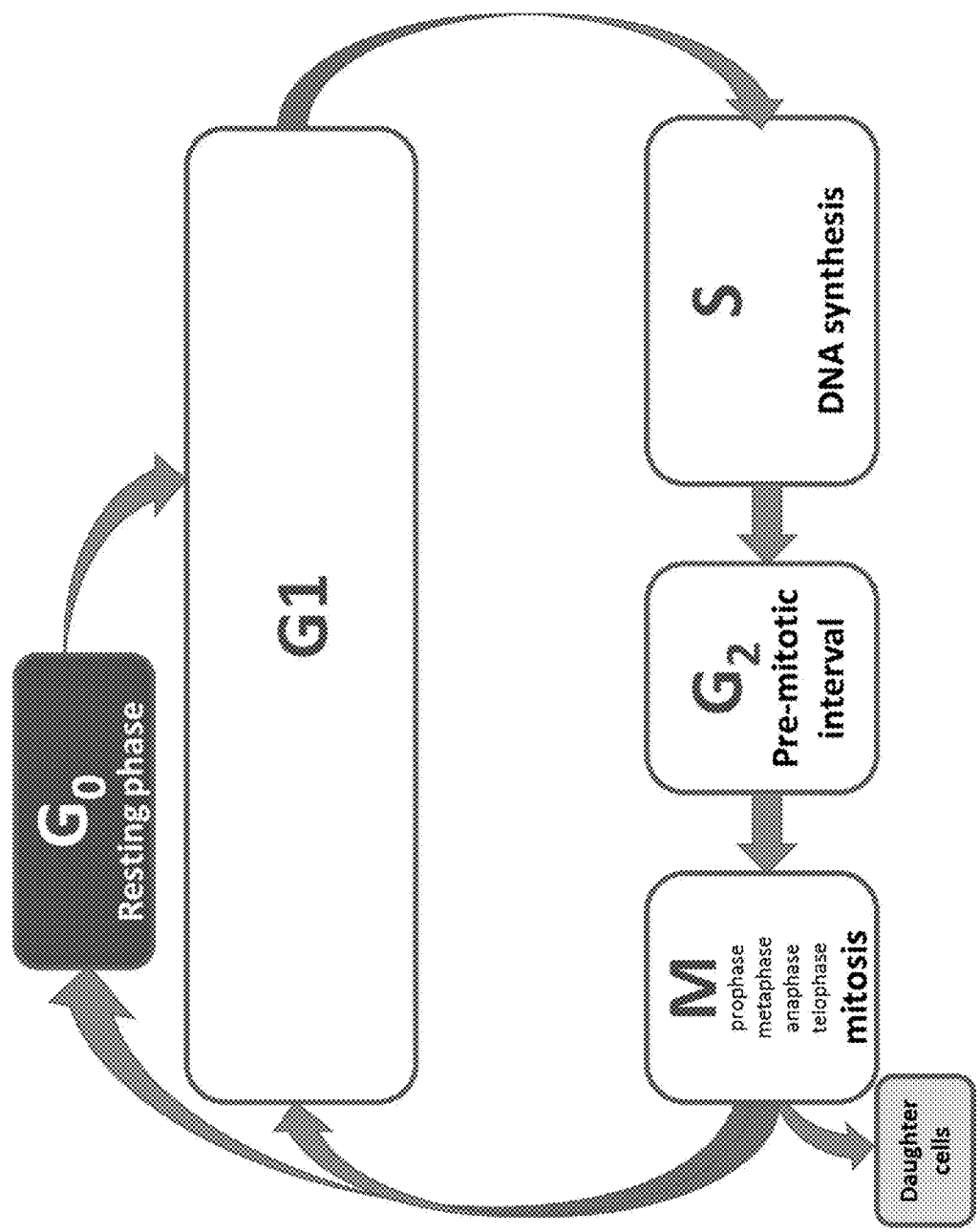
FIG. 1 shows a schematic diagram of a mitotic cycle of a eukaryotic cell.
Figure 2:
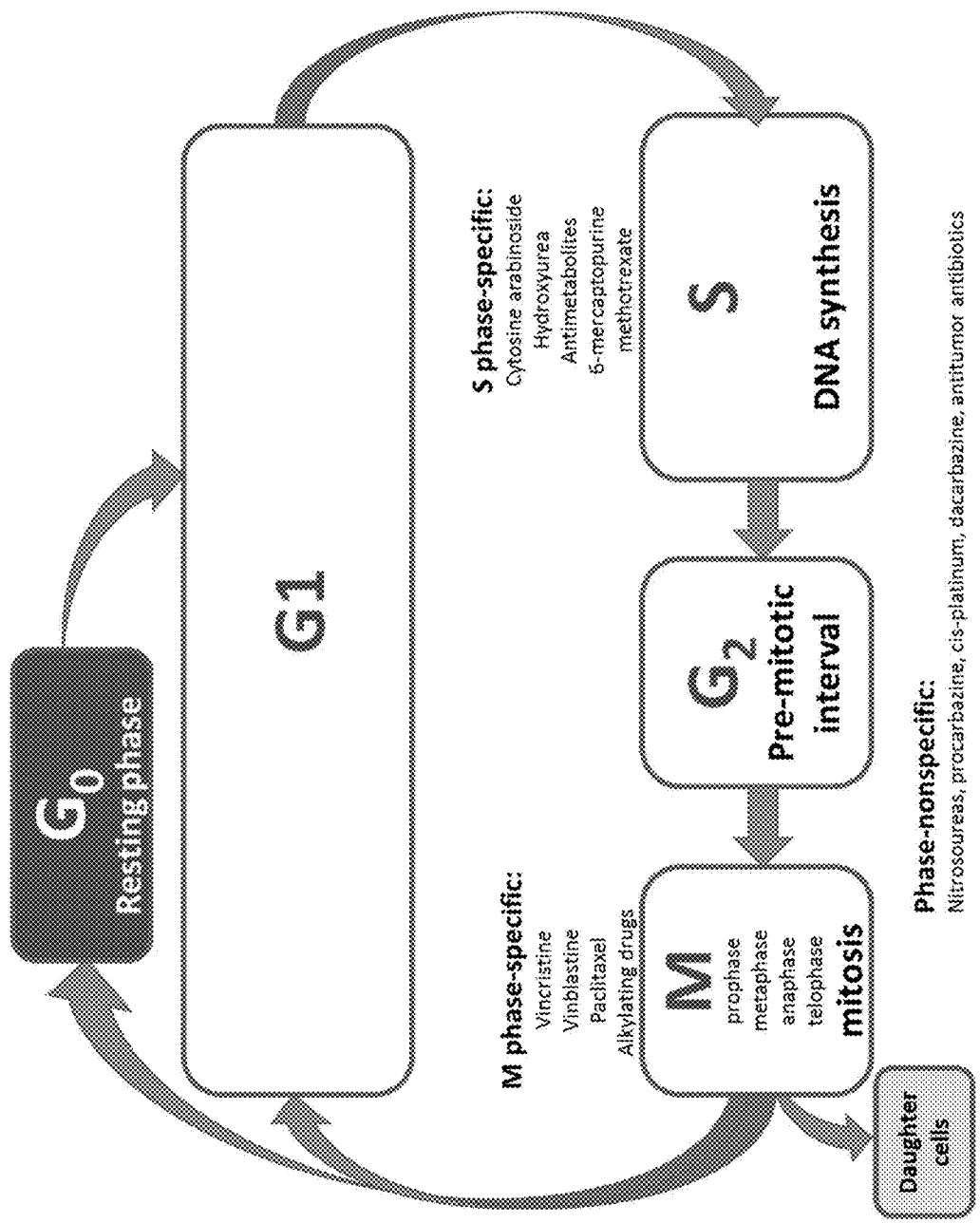
FIG. 2 shows a schematic diagram of a mitotic cycle of a eukaryotic cancer cell annotated to indicate the stages of the cell cycle upon which the available anti-cancer therapeutic agents are believed act.

In the present invention, an "alkyl" group is a saturated, straight or branched, hydrocarbon group, comprising from 1 to 8 carbon atoms ($C_{1-8}$ alkyl group), in particular from 1 to 6, or from 1 to 4 carbons atoms, unless otherwise indicated. Examples of alkyl groups having from 1 to 6 carbon atoms inclusive are methyl, ethyl, propyl (e.g., n-propyl, iso-propyl), butyl (e.g., tert-butyl, sec-butyl, n-butyl), pentyl (e.g., neo-pentyl), hexyl (e.g., n-hexyl), 2-methylbutyl, 2-methylpentyl and the other isomeric forms thereof. Alkyl groups may be unsubstituted or substituted by at least one group chosen from halogen atoms, cycloalkyl, heterocycloalkyl, aryl, heteroaryl, hydroxyl, alkoxyl, alkenyl, alkynyl, CN, nitro, and amino groups.

In the present invention, an "alkenyl" group is a straight or branched hydrocarbon group comprising at least one double carbon-carbon bond, comprising from 2 to 8 carbon atoms (unless otherwise indicated). Examples of alkenyl containing from 2 to 6 carbon atoms are vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof. Alkenyl groups may be unsubstituted, or substituted by at least one group chosen from halogen atoms, cycloalkyl, heterocycloalkyl, aryl, heteroaryl, hydroxyl, alkoxyl, alkenyl, alkynyl, CN, nitro, and amino groups.

In the present invention, an "alkynyl" group is a straight or branched hydrocarbon group comprising at least one triple carbon-carbon bond, comprising from 2 to 8 carbon atoms. Alkynyl groups may be substituted by at least one group chosen from halogen atoms, cycloalkyl, heterocycloalkyl, aryl, heteroaryl, hydroxyl, alkoxyl, alkenyl, alkynyl, CN, nitro, and amino groups.

In the present invention, an "aryl" group is an aromatic hydrocarbon cycle, comprising from 5 to 14 carbon atoms. Most preferred aryl groups are mono- or bi-cyclic and comprises from 6 to 14 carbon atoms, such as phenyl, alpha-naphtyl, β-naphtyl, antracenyl, preferably phenyl. "Aryl" groups also include bicycles or tricycles comprising an aryl cycle fused to at least another aryl, heteroaryl, cycloalkyl or heterocycloalkyl group, such as benzodioxolane, benzodioxane, dihydrobenzofurane or benzimidazole. Aryl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro and amino groups. In addition, aryl groups may be substituted by adjacent substituents which can, taken together with the carbon atom to which they are attached, form a 5- to 6-membered ring which may contain one or more heteroatom(s) selected from N, O, and S.

In the present invention, a "halogen atom" or "halo" is a Cl, Br, F, or I atom.

In the present invention, an "alkoxyl" group is an alkyl group linked to the rest of the molecule through an oxygen atom, of the formula O-alkyl.

In the present invention, an "amino" group is a $NH_2$, NH-alkyl, or N(alkyl)$_2$ group.

In the present invention, a "heteroaryl" group is an aryl group whose cycle is interrupted by at least one heteroatom, for example a N, O, or S atom, such as thiophene or pyridine. Heteroaryl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro, and amino groups. In addition, heteroaryl groups may be substituted by adjacent substituents which can, taken together with the carbon atom to which they are attached, form a 5- to 6-membered ring which may contain one or more heteroatom(s) selected from N, O, and S.

In the present invention, a "cycloalkyl" denotes a saturated alkyl group that forms one cycle having preferably from 3 to 14 carbon atoms, and more preferably 3 to 8 carbon atoms, such as cyclopropyl, cyclobutyl, cyclopentyl, cyclohexyl, cycloheptyl, and cyclooctyl. cycloalkyl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro and amino groups. In addition, cycloalkyl groups may be substituted by adjacent substituents which can, taken together with the carbon atom to which they are attached, form a 5- to 6-membered ring which may contain one or more heteroatom(s) selected from N, O, and S.

In the present invention, a "heterocycloalkyl" group is a cycloalkyl group comprising at least one heteroatom, such as pyrrolidine, tetrahydrothiophene, tetrahydrofuran, piperidine, pyran, dioxin, morpholine or piperazine. A heterocycloalkyl group may in particular comprise from four to fourteen carbon atoms, such as morpholinyl, piperidinyl, pyrrolidinyl, tetrahydropyranyl, dithiolanyl. heterocycloalkyl groups may be unsubstituted, or substituted by at least one group chosen from halogen atoms, cycloalkyl, heterocycloalkyl, aryl, heteroaryl, hydroxyl, alkoxyl, alkenyl, alkynyl, CN, nitro, and amino groups. In addition, heterocycloalkyl groups may be substituted by adjacent substituents which can, taken together with the carbon atom to which they are attached, form a 5- to 6-membered ring which may contain one or more heteroatom(s) selected from N, O, and S.

As used herein, a "neoplasm" means an abnormal mass of tissue that results from neoplasia. "Neoplasia" means a process of an abnormal proliferation of cells. In some embodiments of the invention, a neoplasm is a solid cancer, or alternately a hematopoietic cancer. The neoplasia may be benign, pre-malignant, or malignant. The term neoplasm encompasses mammalian cancers, in some embodiments, human cancers, and carcinomas, sarcomas, blastomas of any tissue (for example adenocarcinomas, squamous cell carcinomas, osteosarcomas, etc.), germ cell tumors, glial cell tumors, lymphomas, leukemias, including solid and lymphoid cancers, kidney, breast, lung, head and neck, bladder, colon, ovarian, prostate, rectal, pancreatic, stomach, brain, head and neck, skin, uterine, cervical, testicular, esophagus, thyroid, liver cancers, biliary cancer, and cancer of the bone and cartilaginous tissue, including non-Hodgkin's lymphomas (e.g., Burkitt's, Small Cell, and Large Cell lymphomas) and Hodgkin's lymphoma, leukemia, multiple myeloma, and myelodysplastic syndrome.

As used herein, the terms "treat," "treating," or "treatment," mean to counteract a medical condition (e.g., cancer) to the extent that the medical condition is improved according to a clinically-acceptable standard. Improvement in cancer can include: 1) reduced rate of tumor growth (tumor growth inhibition), 2) tumor shrinkage (regression), 3) remission, whether partial or total, 4) reduction in metastases, 5) prolonging progression free survival, and 6) delay or elimination of recurrence. In certain embodiments of the invention, treating includes achieving, partially or substantially, one or more of the following results: partially or totally reducing the cancer mass, or volume, or the malignant cell count; ameliorating or improving a clinical symptom or indicator associated with solid cancers or hematopoietic cancers; delaying, inhibiting, or preventing the progression of solid cancers or hematopoietic cancers; or partially or totally delaying, inhibiting or preventing the onset or development of solid cancers or hematopoietic cancers. "Treatment" also can mean prolonging survival compared to expected survival without treatment or compared to standard of care treatment.

Treating includes prophylactic or preventative treatment. "Prophylactic treatment" refers to treatment before appearance or re-appearance of clinical symptoms of a target disorder to prevent, inhibit, or reduce its occurrence, severity, or progression.

As used herein, an "effective amount" refers to an amount of a therapeutic agent or a combination of therapeutic agents that is therapeutically or prophylactically sufficient to affect the desired improvement in the targeted disorder. Examples of effective amounts typically range from about 0.0001 mg/kg of body weight to about 500 mg/kg of body weight per single administered dose, such doses being administered once or over a period of time. An example range is from about 0.0001 mg/kg of body weight to about 5 mg/kg per dose. In other examples, the range can be from about 0.0001 mg/kg to about 5 mg/kg per single administered dose. In still other examples, effective amounts range from about 0.01 mg/kg of body weight to 50 mg/kg of body weight per single administered dose, or from 0.01 mg/kg of body weight to 0.1 mg/kg, 0.5 mg/kg, 1 mg/kg, 2 mg/kg, 3 mg/kg, 4 mg/kg, 5 mg/kg, 6 mg/kg, 10 mg/kg, 20 mg/kg, 25 mg/kg, 30 mg/kg, or 40 mg/kg of body weight per single administered dose. For agents of known clinical use, an example of an effective dose is that amount approved of by a regulatory agency for treatment of an indication.

As used herein, the term "subject" refers to a mammal, for example a human, but can also mean an animal in need of veterinary treatment, e.g., companion animals (e.g., dogs, cats, and the like), farm animals (e.g., cows, sheep, pigs, horses, and the like), and laboratory animals (e.g., rats, mice, guinea pigs, and the like).

As used herein, the term "therapeutic agent" means any chemical molecule used or contemplated for use or investigated for use in cancer treatment, including cytotoxic, cytostatic, or targeted agents, whether small molecules, or peptides, or antibodies, or oligonucleotides, irrespective of mechanism of action. As used herein, the terms "therapeutic" or "therapeutic agent" refer to either the active pharmaceutical ingredient (API) or its pharmaceutically acceptable salt or hydrate (solvate), or a drug product containing the therapeutic agent, however formulated, and whether API is amorphous or crystalline and of whatever polymorphic form. Formulation means a combination of an active pharmaceutical ingredient (API, drug substance) or ingredients (APIs) combined with excipients and/or delivery vehicle to make an administrable dosage form (drug product).

A reference to a biologic drug substance, for example cetuximab, means any drug product containing that biologic or its biosimilar, produced, characterized, and defined as a biosimilar by persons skilled in the art and by the regulatory agencies.

The therapeutic agents of the invention are generally administered with a pharmaceutically acceptable carrier, with respect to standard pharmaceutical practice (such as described in *Remington: The Science and Practice of Pharmacy*, 21$^{st}$ Edition, Lippincott Williams & Wilkins). Accordingly, a further object of this invention relates to a pharmaceutical compositions defined herein and pharmaceutically acceptable carriers.

As used herein, the term "inhibitor" means any composition that reduces the activity of an enzyme. An example of an inhibitor is a chemical molecule. A measure of the potency of an inhibitor is its "50% inhibitory concentration" ($IC_{50}$). $IC_{50}$ concentration or $IC_{50}$ value is the concentration of an inhibitor at which 50% of the enzymatic activity is inhibited by the inhibitor. Methods for the determination of $IC_{50}$ values, for example, of kinase inhibitors are known to persons of ordinary skill in the art and include direct and indirect functional assays, such as the HotSpot™ kinase assay technology (Reaction Biology Corporation, Malvern, Pa., www.reactionbiology.com) or competition binding assays, such as KINOMEscan® (DiscoverX Corporation, Freemont, Calif., www.discoverx.com).

A measure of the potency of a therapeutic agent against a cell line is its "50% effective concentration" ($EC_{50}$). $EC_{50}$ value is the concentration of a drug that produces half-maximal response, such as, for example, 50% cell growth inhibition or 50% reduction in cell viability. Methods for the determination of $EC_{50}$ values, for example, of kinase inhibitors are known to persons of ordinary skill in the art.

As used herein, the term "quiescence" or "quiescent state" refers to the $G_0$ state of the cell cycle, as understood by the practitioners of the art.

As used herein, the term "therapeutic agent effective against quiescent cancer cells" refers to a molecule that either reduces the fraction of quiescent cancer cells in a cell population or prevents, completely or substantially, an increase in fraction of quiescent cancer cells in a population under conditions that otherwise would lead to such an increase.

A "quiescent neoplastic cell", alternately referred to as a "quiescent cancer cell" means a cancer cell that exists in the quiescent, or $G_0$, state of the cell cycle. A "fraction of quiescent neoplastic cells" or "fraction of quiescent cancer cells", as used herein, means the portion of a cancer cell population that exists in the $G_0$ state of the cell cycle. Determining the fraction of quiescent neoplastic cells includes characterizing a cell population by distribution of its constituent cells within the stages of the cell cycle. The fraction of cells in the $G_0$ state (i.e., quiescent neoplastic cells) is quantified relative to the total cell population. The fraction may be expressed as a percentage of the total cell population (i.e. (number of quiescent cells divided by total cells in cell population) multiplied by 100). Characterization of the cell population by distribution of its constituent cells within the stages of the cell cycle may be achieved by techniques known to persons of ordinary skill in the art, and may include analysis by DNA and/or RNA content distribution within the cell cycle using flow cytometry methods, for example, fluorescence-activated cell sorting (FACS).

As used herein, the terms "EGFR inhibitor", and "EGFR tyrosine kinase inhibitor", and "EGFR TK inhibitor" are equivalent and may be used interchangeably. Examples EGFR inhibitors include both reversible and irreversible small molecule inhibitors. For example, reversible EGFR inhibitors include brigatinib, erlotinib, gefitinib, icotinib, lapatinib, MTKi-327 (JNJ-26483327), sapitinib, vandetanib, and varlitinib and irreversible EGFR inhibitors include afatinib, canertinib, dacomitinib, neratinib, osimertinib, pelitinib, TAK285, rociletinib, WZ4002.

DETAILED DESCRIPTION

The present invention provides compositions and methods for the treatment of neoplasms, in particular, by targeting of quiescent cancers cells with therapeutic agents in combination with other treatments effective against certain neoplastic conditions, in particular, anti-cancer treatment with EGFR inhibitor therapeutic agents.

Generally, the invention features a method of treating a neoplasm comprising: administering to a subject in need thereof a therapeutically effective amount of (a) a therapeutic agent effective against quiescent cancer cells; and (b) second agent which is an EGFR inhibitor, wherein the two agents can be administered sequentially or concomitantly. In some embodiments, the neoplasm is a cancer or a population of cancer cells in vitro or in vivo. In some embodiments, the subject receiving the treatment is diagnosed with cancer (e.g., metastatic or pre-metastatic). In some embodiments, the subject has been treated previously with a first-line therapy against cancer. In some embodiments, the subject has been treated previously with second-line and/or other therapies. In some embodiments, the subject is treated, or has been treated, with radiation therapy. In some embodiments, the subject was treated with surgery, for example, to resect or debulk a tumor. In other embodiments, the subject's neoplasm has recurred. In some embodiments, the subject is treated, or has been treated, with two or more EGFR inhibitors sequentially or concomitantly.

In some embodiments, the combined treatment may result in improved outcomes, such as increased survival, reduction of severity, delay or elimination of recurrence, or reduced side effects of the primary treatments (i.e., the EGFR inhibitor). In some embodiments, the second agent is administered at lower dose and/or for a shorter duration when administered as part of the combination as compared to a treatment with the agent alone. For example, in some embodiments, the $EC_{50}$ value of the EGFR inhibitor is at least 20%, 25%, 30%, 40%, 50% lower in the combination treatment when compared to the same treatment with the EGFR inhibitor as a single agent, as determined, for example, in cell-based assays. In some embodiments, the combination treatment increases fraction of apoptotic cells in a treated population as compared to either agent alone, by at least by 2-fold, 3-fold, 4-fold, 5-fold as determined, for example, by fraction of sub-$G_0$ phase cells in a FACS assay. In some embodiments, the fraction of quiescent cancer cells is decreased by at least 20%, 25%, 30%, 40%, 50% or more in the combination treatment when compared to the same treatment with the EGFR inhibitor as a single agent, as determined, for example, in cell-based assays.

In one embodiment, the therapeutic agent effective against quiescent cancer cells is a DYRK1 inhibitor. In some embodiments, the DYRK1 inhibitor is a compound that inhibits activity of a DYRK1 kinase, either DYRK1A or DYRK1B (in vitro or in vivo), for example, with an $IC_{50}$ value of <100 nM, <90 nM, <80 nM, <70 nM, <60 nM, <50 nM, <40 nM, <30 nM, <20 nM, <10 nM, <5 nM or lower in biochemical assays. In some embodiments, the DYRK1 inhibitor reduces the fraction of quiescent cancer cells (in vitro or in vivo) in a population or a tumor that would otherwise be found in the absence of such inhibitor, for example, by at least 5%, 10%, 15%, 20%, 25%, 30%, 40%, 50%, or more.

In some embodiments, the DYRK1 inhibitor inhibits both DYRK1A and DYRK1B. In some embodiments, the DYRK1 inhibitor is selective for DYRK1A, with ratio of DYRK1B $IC_{50}$ to DYRK1A $IC_{50}$ of 1000, 100, 50, 25, 10 to 1. In some embodiments, the DYRK1 inhibitor is selective for DYRK1B, with ratio of DYRK1A $IC_{50}$ to DYRK1B $IC_{50}$ of 1000, 100, 50, 25, 10 to 1. In some embodiments, the DYRK1 inhibitor is selective for DYRK1 by at least 4-fold, 5-fold, 10-fold, 20-fold, 50-fold, 100-fold as compared to DYRK2 and/or DYRK3 and/or DYRK4, as determined by ratios of $IC_{50}$ values. In some embodiments, the DYRK1 inhibitor is selective for DYRK1 by at least 4-fold, 5-fold, 10-fold, 20-fold, 50-fold, 100-fold, 500-fold, 1000-fold as compared to cyclin dependent kinases (CDKs) such as, for example, CDK2, as determined by ratios of $IC_{50}$ values.

Examples of known DYRK1 inhibitors include AZ191, DYRKi, harmine, ID-8, leucettine L41, NCGC00185981, INDY, ProINDY, TC-S 7004, and TG003. At least one known DYRK1 inhibitor, TC-S 7004, (US20120184562) is reported to be effective against quiescent cancer cells in vitro (Ewton D Z, Hu J, Vilenchik M, Deng X, Luk K C, Polonskaia A, Hoffman A F, Zipf K, Boylan J F, and Friedman E A. (2011) Inactivation of MIRK/DYRK1B kinase targets quiescent pancreatic cancer cells. Molecular Cancer Therapeutics 10: 2104-2114).

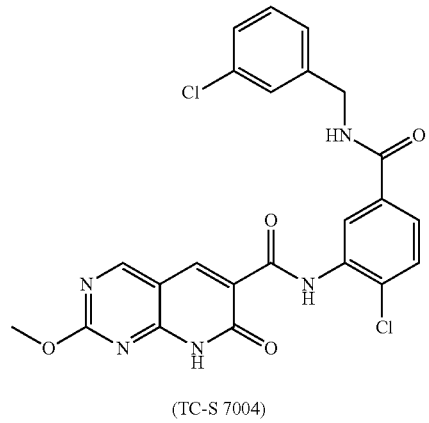

(TC-S 7004)

In one embodiment, the DYRK1 inhibitor is a compound of formula I:

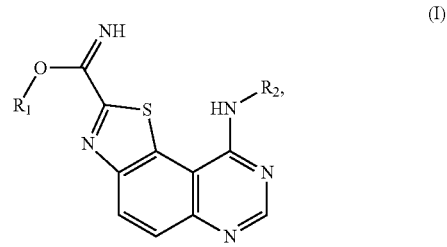

or a pharmaceutically acceptable salt or solvate thereof, wherein, $R_1$ is a substituted or unsubstituted $C_{1-8}$ alkyl, a substituted or unsubstituted phenyl, or a substituted or unsubstituted benzyl;

R$_2$ is phenyl, optionally substituted with up to four groups independently selected from halo, CN, NO$_2$, NHC(O)C$_{1-4}$ alkyl, C$_{1-4}$ alkyl, OH, OC$_{1-4}$ alkyl, wherein two adjacent groups and their intervening carbon atoms may form a 5- to 6-membered ring containing one or more heteroatoms selected from N, O, or S.

In one embodiment, the compound of formula I is selected from:

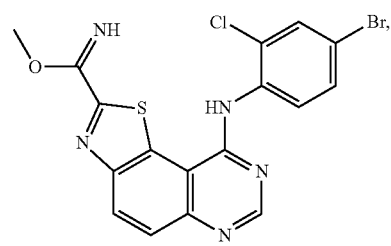
(I-1)

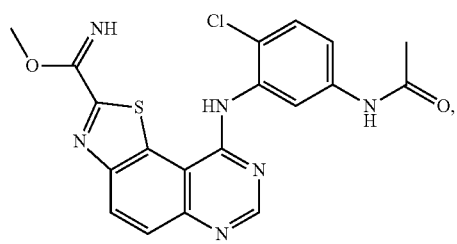
(I-2)

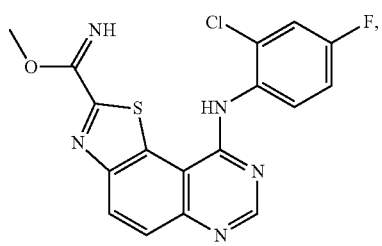
(I-3)

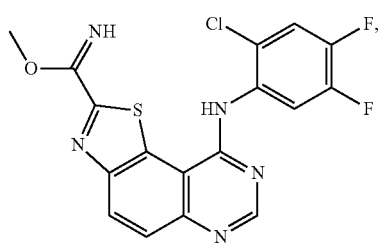
(I-4)

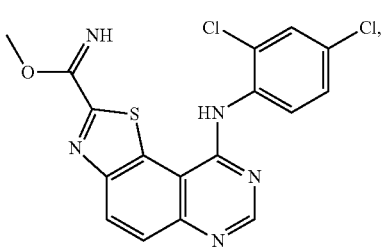
(I-5)

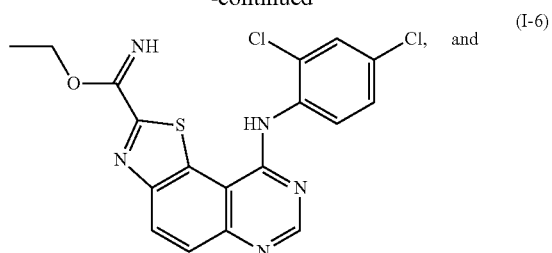
(I-6)

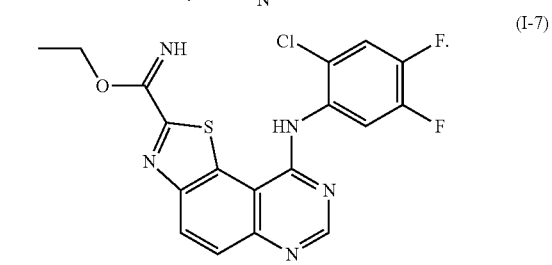
(I-7)

In another embodiment, the methods of the invention further provide (c) administering to the subject another cancer therapy, for example, radiation therapy or other cancer treatment.

In one embodiment, the methods of the invention comprise: administering to a subject in need thereof a therapeutically effective amount of (a) a therapeutic agent of formula I; (b) an EGFR inhibitor; and (c) radiation therapy; each therapy being administered sequentially or concomitantly. For example, in some embodiments, the subject is first treated with radiation therapy, whereupon the subject is administered a therapeutic agent of Formula I, alone or in combination with the EGFR inhibitor. In some embodiments, the subject is co-administered (a) the therapeutic agent effective against quiescent cancer cells, (b) the EGFR inhibitor and optionally (c) the radiation therapy. In some embodiments, the EGFR inhibitor is a compound that inhibits activity of wild type, or a mutant, or a truncated EGFR tyrosine kinase (in vitro or in vivo), for example, with the IC$_{50}$ of <100 nM, <90 nM, <80 nM, <70 nM, <60 nM, <50 nM, <40 nM, <30 nM, <20 nM, <10 nM, <5 nM, or lower in biochemical assays. In some embodiments, the EGFR inhibitor is 4-fold, 5-fold, 10-fold, 20-fold, 50-fold, 100-fold, 1000-fold selective for EGFR compared to HER2/c-neu (ErbB-2), Her 3 (ErbB-3), and Her 4 (ErbB-4). In some embodiments, the EGFR inhibitor also inhibits one or more of HER2/c-neu (ErbB-2), Her 3 (ErbB-3), and Her 4 (ErbB-4) with an IC$_{50}$ value of <100 nM, <90 nM, <80 nM, <70 nM, <60 nM, <50 nM, <40 nM, <30 nM, <20 nM, <10 nM, <5 nM, or lower in biochemical assays. In some embodiments, the EGFR inhibitor also inhibits one or more of the histone deacetylases (HDAC), such as HDAC of Class I, Class II, Class III, and/or Class IV with an IC$_{50}$ value of <100 nM, <90 nM, <80 nM, <70 nM, <60 nM<50 nM, <40 nM, <30 nM, <20 nM, <10 nM, <5 nM, or lower in biochemical assays. In some embodiments, the EGFR inhibitor is selective for the mutated EGFR, for example EGFR harboring T790M mutation, compared with the wild type EGFR. In some embodiments, the EGFR inhibitor is an EGFR inhibitor effective to treat or prevent a neoplasm, including but not limited to, all such compounds approved for the treatment of cancer, compounds in clinical trials for the treatment of cancer, compounds that otherwise demonstrate efficacy in treating cancer in mammalian subject (e.g., mouse, rats, dogs, monkeys, humans), and compounds that demonstrate efficacy against neoplastic cells in vitro. Many such compounds are known.

The EGFR inhibitor can be, for example, a small molecule or an anti-EGFR antibody.

In one embodiment, the EGFR inhibitor is a reversible EGFR tyrosine kinase inhibitor (EGFR TKI). In a further embodiment, the reversible EGFR TKI is, for example, brigatinib, CUDC-101, erlotinib, gefitinib, icotinib, lapatinib, sapitinib, vandetanib, varlitinib, tesevatinib, and Tyrphostin AG 1478. In yet another embodiment, the reversible EGFR TKI is AZD3759 or MTKi-327 (JNJ-26483327). In some embodiments, the reversible EGFR TKI is not erlotinib or lapatinib.

In another embodiment, the EGFR inhibitor is an irreversible EGFR TKI. In a further embodiment, the irreversible EGFR inhibitor is, for example, afatinib, olmutinib (HM61713), canertinib, CL-387785 (EKI-785), CNX-2006, dacomitinib, naquotinib (ASP8273), neratinib, osimertinib, PD168393, pelitinib, poziotinib, rociletinib, TAK285, and WZ4002. In yet another embodiment, the irreversible EGFR TKI is, for example, allitinib (ALS-1306; AST-1306), AV-412 (MP-412), nazartinib (EGF816), and pyrotinib.

In yet another embodiment, the EGFR inhibitor is an antibody against EGFR, for example, cetuximab (Erbitux®) and panitumumab (Vectibix®).

In another embodiment, the neoplasm being treated is a cancer, for example, biliary cancer, brain cancer, breast cancer, cervical cancer, colon cancer, gastric cancer, kidney cancer, head and neck cancer, leukemia, liver cancer, non-small cell lung cancer, small cell lung cancer, lymphoma, ovarian cancer, pancreatic cancer, prostate cancer, rectal cancer, sarcoma, skin cancer (e.g. melanoma), testicular cancer, thyroid cancer, or uterine cancer. In a further embodiment, the cancer is non-small cell lung cancer, pancreatic cancer, and head and neck cancer. In further embodiments, the cancer is primary or metastatic. In yet further embodiments, the cancer is of the type represented by the cell line types shown in the Examples. In some embodiments, the subject having cancer possesses a mutation in the EGFR gene associated with an increased risk of cancer and/or resistance to certain EGFR TKIs.

The embodiments described here are illustrative and are not meant to be limiting with regard to additional combination components, routes and order of administration, patient type (previously untreated or previously treated, absence or presence of co-morbid conditions, age, sex, etc.), or stage of patient's disease, type of EGFR inhibitor, etc.

EGFR inhibitors are known in the art (Lee C C, et al. (2014) Small-molecule EGFR tyrosine kinase inhibitors for the treatment of cancer, *Expert Opinion on Investigational Drugs* 23, 1333-1348). These drugs are used to treat patients whose cancers harbor EGFR activating mutations or other EGFR abnormalities (overexpression, etc.), most importantly non-small cell lung cancer (NSCLC) as well as pancreatic, breast, and head and neck cancers. Clinically used EGFR inhibitors provide significant benefits to the patients, especially in terms of progression-free survival. However, most patients whose cancers respond to the initial treatment with EGFR inhibitors do suffer a relapse within a short period of time, 1-2 years. Moreover, their cancers become resistant to the initially effective treatments. Mutations in the EGFR protein explain some of this resistance and new EGFR inhibitors have become available that target the mutated EGFRs, especially the T790M mutation.

Recently, it was discovered that exposure of PC9 human non-small cell lung cancer cells to reversible EGFR inhibitors erlotinib or lapatinib results in pharmacological quiescence, i.e. a significant increase of fraction of cells in $G_0$ (Tyson D R, Garbett S P, Frick P L, et al. (2012) Fractional proliferation: a method to deconvolve cell population dynamics from single-cell data, *Nature Methods* 9, 923-928). In vitro, the anti-proliferative response to treatment with erlotinib of the PC9 cells, which are hypersensitive to EGFR TK inhibitors, is due primarily to the entry of cells into the quiescent state and not to apoptosis.

It was found that exposure of different cancer cell lines to $2^{nd}$ and $3^{rd}$ generation EGFR TKIs, including irreversible inhibitors, whether based on an anilino-quinazoline or anilino-pyrimidine scaffold, resulted in a large increases in $G_0$ fraction. Therefore, the increase in cells in $G_0$ (quiescent cells) is a general property of the EGFR tyrosine kinase inhibitors and is not limited to the few specific examples reported previously, which was unanticipated and unexpected. The increases in populations of cells in $G_0$ on exposure to EGFR TKIs were more pronounced than those induced by serum starvation, an unexpected observation. Consequently, the EGFR TKIs induce pharmacological quiescence. This cytostatic effect may, at least in part, account for the clinical observations with EGFR inhibitors of temporary cancer remission followed by recurrence.

A $G_0$ state is maintained by a specific program of gene expression. Evidence is emerging that DYRK1 kinases such as DYRK1A and DYRK1B may be important for the maintenance of cancer cells in $G_0$ state (quiescent state) in cancer cells.

DYRK1B/Mirk is a member of the Minibrain/DYRK family of kinases which mediates survival and differentiation in certain normal tissues. (Kentrup H, Becker W, Heukelbach J, Wilmes A, Schurmann A, Huppertz C, Kainulainen H, and Joost H G (1996) Dyrk, a dual specificity protein kinase with unique structural features whose activity is dependent on tyrosine residues between subdomains VII and VIII, *Journal of Biological Chemistry* 271, 3488-3495; Becker W, Weber Y, Wetzel K, Eirmbter K, Tejedor F J, and Joost H G (1998) Sequence characteristics, subcellular localization, and substrate specificity of DYRK-related kinases, a novel family of dual specificity protein kinases, *Journal of Biological Chemistry* 273, 25893-25902). DYRK1B is expressed at detectable levels in skeletal muscle cells and testes. Knockout of DYRK1B caused no evident abnormal phenotype in mice even in developing muscle, suggesting that DYRK1B is not an essential gene for normal development. Supporting this interpretation, normal fibroblasts exhibited no alteration in survival after 20-fold depletion of DYRK1B kinase levels. Thus, DYRK1B does not appear to be an essential gene for survival of normal cells yet there is evidence that it is upregulated in certain malignant cancer cells in which DYRK1B is believed to mediate survival by retaining cancer cells in quiescent state. These unusual characteristics suggest that DYRK1B may be an attractive target for therapeutic intervention and in particular for anti-cancer therapy directly against quiescent cancer cells.

The disclosed combinations and methods may afford one or more of the improvements as defined in the Glossary relative to the use of each individual components or existing single and combination treatments. Also, the disclosed combinations and methods may permit reduction in doses and/or frequency of administration of therapeutic agents and radiation to achieve the same improvements as a result of treatment relative to what is possible using individual components or existing single and combination treatments.

The disclosed combinations need not be synergistic or even result in a significant reduction in $EC_{50}$ values to yield a significant improvement in the effectiveness of treatment relative to single therapy with an EGFR inhibitor. As discussed above, quiescent cancer cells are inherently less susceptible to anti-cancer therapeutics, including EGFR inhibitors, and even a small fraction of quiescent cells that survives post treatment can lead to recurrence. Consequently, eradicating the resistant, quiescent cell populations in a neoplasm may or may not yield a synergistic reduction in $EC_{50}$ values yet may yield a significant improvement in cancer recurrence rate and appearance of metastatic neoplasms.

The administration routes and regimen of the disclosed combination may well vary depending on the neoplastic condition treated, extent of progression of the neoplasm, age and physical condition of the subject, exact combination selected, and other factors. Administration regimen may include multiple doses per period of time, the treatments administered concurrently or sequentially, etc. For example, therapeutic agent effective against quiescent cancer cells may be administered before the EGFR inhibitor. The therapeutic agent effective against quiescent cancer cells may be administered 6 hours, 12 hours, 24 hours, 48 hours, 72 hours, 96 hours before the EGFR inhibitor. The therapeutic agent effective against quiescent cancer cells may be administered at the same time (concomitantly) as the EGFR inhibitor. The therapeutic agent effective against quiescent cancer cells may be administered 6 hours, 12 hours, 24 hours, 48 hours, 72 hours, 96 hours after the EGFR inhibitor. The therapeutic agent effective against quiescent cancer cells and/or the EGFR inhibitor may be administered before, after, or concomitantly with radiation or other therapy.

The therapeutic agent effective against quiescent cancer cells may be administered daily, every two days, every three days, every four days, biweekly (twice per week), once weekly, once every two weeks, once per month by oral (PO), intravenous (IV), intraperitoneal (IP), subcutaneous (SC), intratumoral (IT), intrathecal, or other routes of administration.

The combinations may be administered to subjects who are naive to treatment (have not been treated), or subjects who underwent previous treatments with first-line, second-line, third-line, or other therapies, radiation treatments, or have undergone surgical resection or debulking of a solid tumor, or subjects whose cancers relapsed, or subjects whose cancers are non-metastatic or metastatic.

EXAMPLES

The following examples are not intended to be limiting. Those of skill in the art will, in light of the present disclosure, appreciate that many changes can be made in the specific materials and which are disclosed and still obtain a like or similar result without departing from the spirit and scope of the invention.

Example 1

Determination of Fraction of Quiescent Cancer Cells Within a Population

The following cell lines were obtained from ATCC and cultured according to the ATCC recommendations: H1975—non-small cell lung cancer cell line harboring L858R and T790M mutations; HCC827—non-small cell lung cancer cell line with E746-A750 deletion in EGFR TK; PC9—non-small cell lung cancer cell line with E746-A750 deletion in EGFR TK; A549—non-small cell lung cancer cell line with wild type EGFR; PANC1—pancreatic cancer cell line; MiaPaCa-2—pancreatic cancer cell line, and SW620—colon cancer cell line. Cell cultures of these lines were seeded into 6-well plates at $3\times10^5$–$6\times10^5$ cells/well; the plated number of cells depended on cell size and rate of proliferation, aiming for approximately 50% confluency. After seeding, the cells were allowed to attach for 24 hours while incubated at 37° C. in a humidified 5% $CO_2$ atmosphere, and then treated with compounds for desired amount of time (usually 24 hours) incubating under same conditions. Then the cells were harvested by trypsinization, pooled with the floating cells, washed in PBS, and fixed in 70% ice-cold ethanol overnight. For Acridine Orange (AO) staining, fixed cells were washed once with ice-cold PBS, re-suspended in 100 μL PBS, followed by addition of 200 μL of permeabilizing solution and 600 μL AO staining solution. The measurements were performed with Guava easyCyte HT flow cytometer (EMD Millipore) using the blue laser for excitation at 488 nm, monitoring emission of the AO-DNA complex at 526 nm and AO-RNA complex at 650 nm. The complete protocol and composition of buffers are described in the literature (Darzynkiewicz Z, Juan G, and Srour E F (2004) Differential Staining of DNA and RNA (2004). *Current Protocols in Cytometry*, Chapter 7: Unit 7.3).

Example 2

General Procedure for the Cell Viability Assays in 2D Cell Culture

For viability analysis, cells were seeded into 96-well plates at $2\times10^3$-$6\times10^3$ cells/well; depending on cell size and rate of proliferation aiming for approximately 50% confluency. Cells were allowed to attach for 24 hours incubated at 37° C. in a humidified 5% $CO_2$ atmosphere. The treatments were performed using at least 6 different concentrations of a compound in 1:3 serial dilutions. Before reading the results cells were incubated for 96 hours in 5% $CO_2$ incubator at 37° C. Each treatment was performed in triplicate. Results were analyzed by CellTiter-Glo™ Luminescent Cell Viability Assay (Promega, cat. # G7571) according to the manufacturer's instructions using SpectraMAX Gemini Spectrophotometer (Molecular Devices).

Example 3

Figure 3:
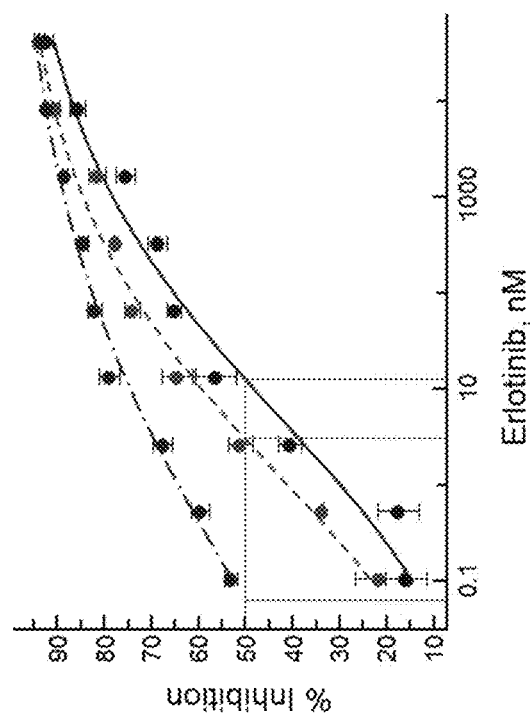
FIG. 3 shows effect of combination of erlotinib and Compound I-5 (0, 2.5, and 5 µM) on the growth of HCC827 cells.

Combination of a Molecule Effective Against Quiescent Cancer Cells With Erlotinib HCC827 cells were cultured and treated as described in Examples 1 and 2. The highest concentration of erlotinib used in this assay was 40 nM and the concentrations of Compound I-5 were 2 μM and 4 μM. The observed $EC_{50}$ values for erlotinib were 12.15 nM when Compound I-5 was not present, 2.95 nM when Compound I-5 was present at a concentration of 2 μM and <0.1 nM when Compound I-5 was present at a concentration of 4 μM. See FIG. 3.

Figure 4:
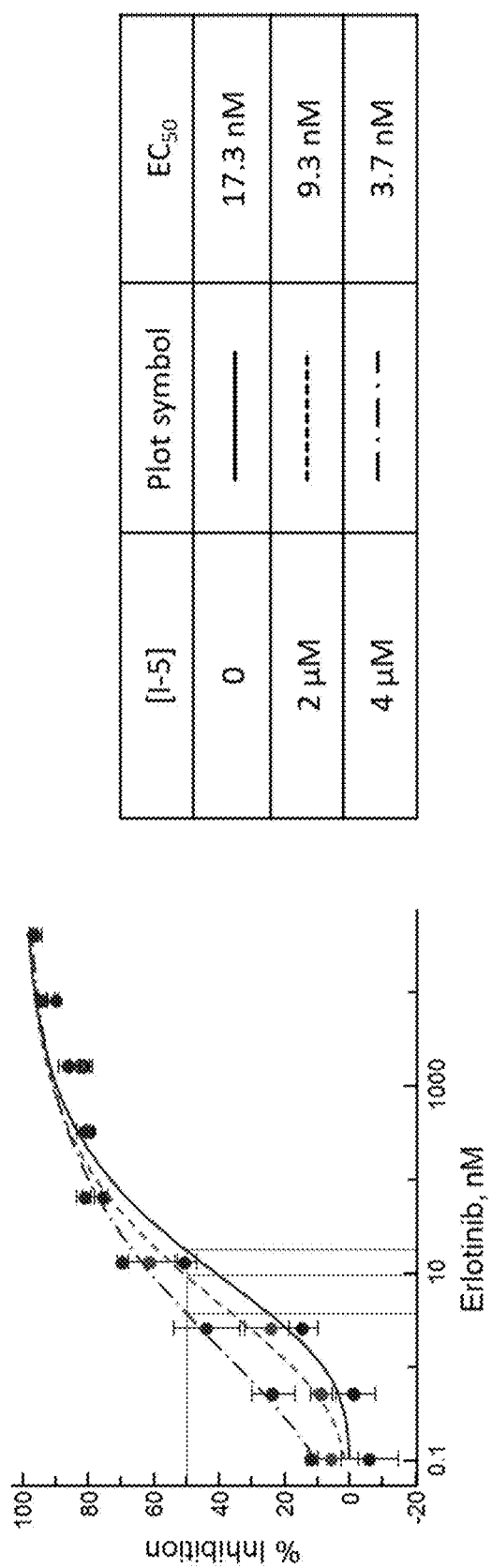
FIG. 4 shows the effect of combination of erlotinib and Compound I-5 (0, 2, and 5 µM) on the growth of PC9 cells.

PC9 cells were cultured and treated as described in Examples 1 and 2. The highest concentration of erlotinib used in this assay was 40 nM and the concentrations of Compound I-5 were 2 μM and 4 μM, respectively. The $EC_{50}$ values observed for erlontinib were 17.3 nM when Compound I-5 was not present, 9.3 nM when Compound I-5 was present at a concentration of 2 and 3.7 nM when Compound I-5 was present at a concentration of 4 μM. See FIG. 4.

Figure 5:
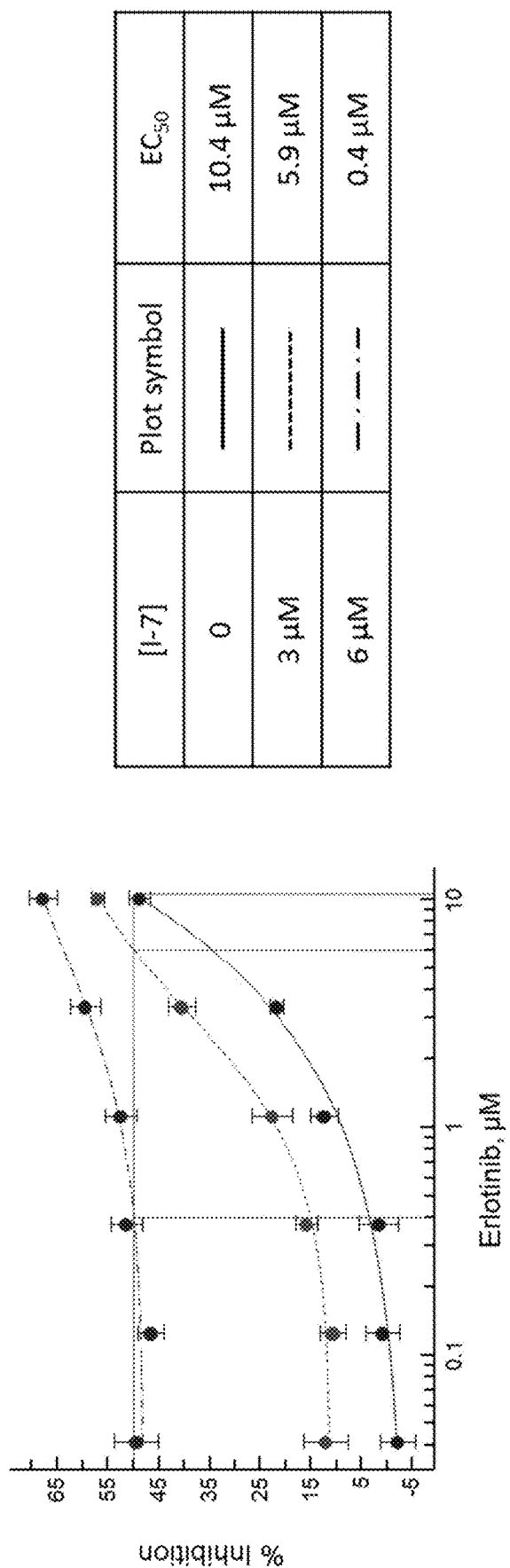
FIG. 5 shows the effect of combination of erlotinib and Compound I-7 (0, 3, and 6 µM) on the growth of A549 cells.

A549 cells were cultured and treated as described in Examples 1 and 2. The highest concentration of erlotinib used in this assay was 10 µM and the concentrations of Compound I-7 were 3 µM and 6 µM, respectively. The $EC_{50}$ values observed for erlontinib were 10.4 µM when Compound I-7 was not present, 5.9 µM when Compound I-7 was present at a concentration of 3 µM, and 0.4 µM when Compound I-7 was present at a concentration of 6 µM. See FIG. 5.

Figure 6:
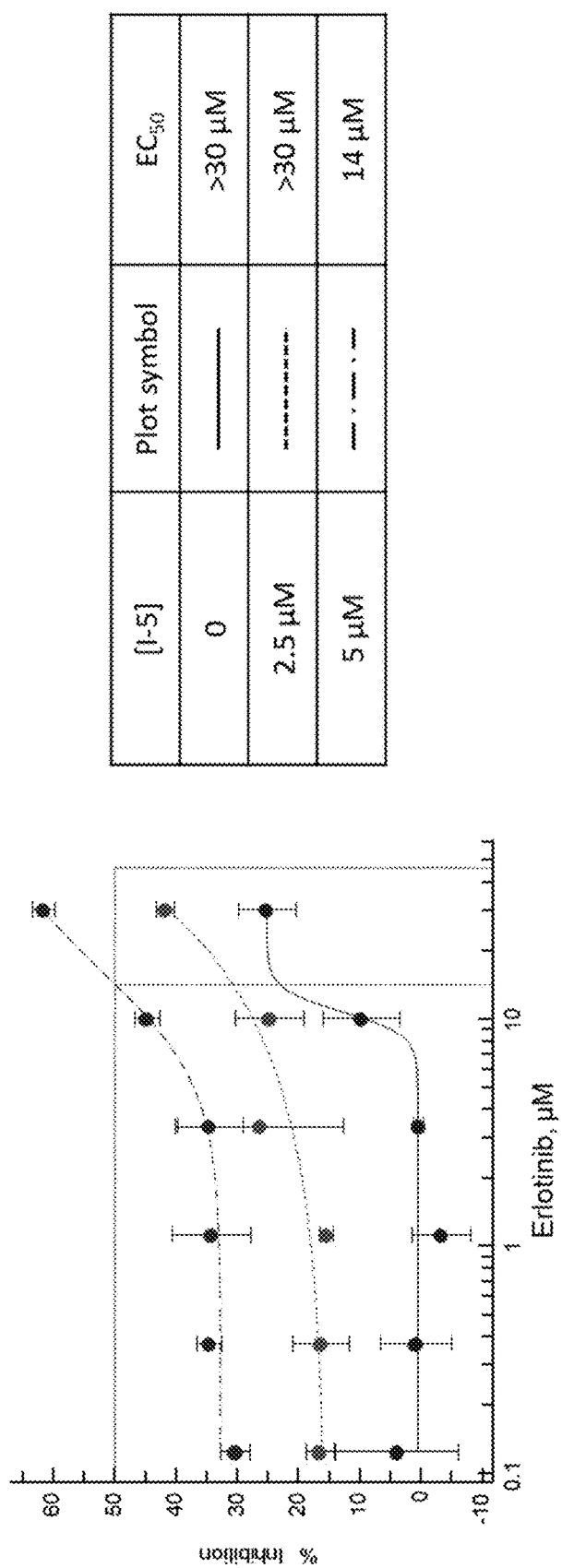
FIG. 6 shows the effect of combination of erlotinib and Compound I-5 (0, 2.5, and 5 µM) on the growth of PANC1 cells.

PANC1 cells were cultured and treated as described in Examples 1 and 2. The highest concentration of erlotinib used in this assay was 30 µM and the concentrations of Compound I-5 were 2.5 µM and 5 µM, respectively. The $EC_{50}$ values observed for erlontinib were >30 µM when Compound I-5 was not present, >30 µM when Compound I-5 was present at a concentration of 2.5 µM, and 14 µM when Compound I-5 was present at a concentration of 5 µM. See FIG. 6.

Figure 7:
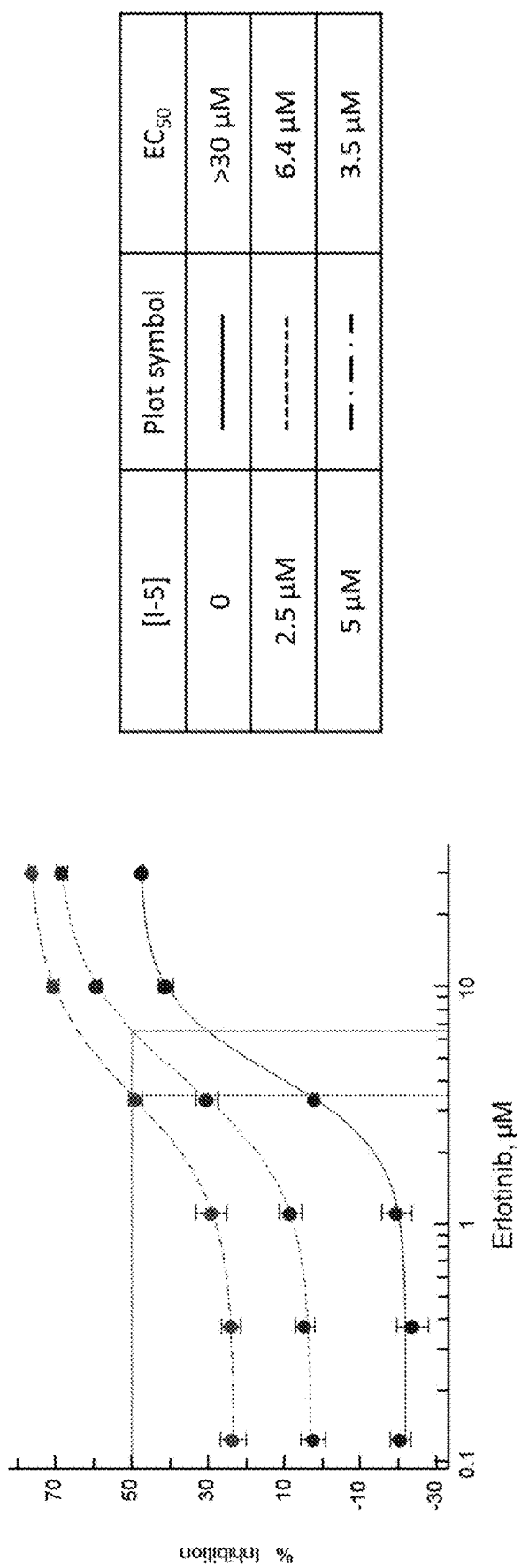
FIG. 7 shows the effect of combination of erlotinib and Compound I-5 (0, 2.5, and 5 µM) on the growth of MiaPaCa-2 cells.

MiaPaCa-2 cells were cultured and treated as described in Examples 1 and 2. The highest concentration of erlotinib used in this assay was 30 µM and the concentrations of Compound I-5 were 2.5 µM and 5 µM, respectively. The $EC_{50}$ values observed for erlontinib were >30 µM when Compound I-5 was not present, 6.4 µM when Compound I-5 was present at a concentration of 2.5 µM, and 3.5 µM when Compound I-5 was present at a concentration of 5 µM. See FIG. 7.

In these experiments it was demonstrated that combining a reversible EGFR inhibitor erlotinib with Compound I-5 yielded a significant increase in cytotoxicity (decrease in $EC_{50}$ value) of erlotinib against HCC827, PC9, and A549 non-small cell lung cancer cell lines. Further, a significant increase in cytotoxicity (lower $EC_{50}$ value) was observed against PANC1 and MiaPaCa-2 pancreatic cancer cell lines. This result is especially unexpected for MiaPaCa-2 cell line, which has comparatively low expression of EGFR.

Example 4

Figure 8:
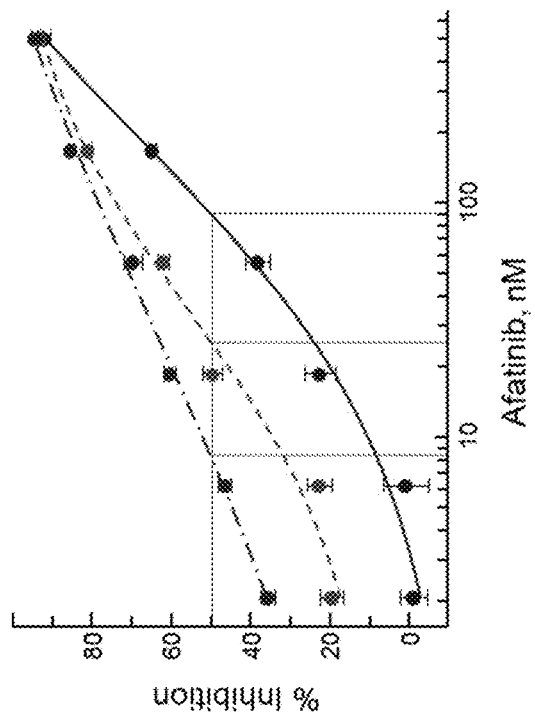
FIG. 8 shows the effect of combination of afatinib and Compound I-7 (0, 2, and 4 µM) on the growth of H1975 cells.

Combination of a Molecule Effective Against Quiescent Cancer Cells With Afatinib H1975 cells were cultured and treated as described in Examples 1 and 2. The highest concentration of afatinib used in this assay was 500 nM and the concentrations of Compound I-7 were 2 µM and 4 µM. The $EC_{50}$ values observed for afatinib were 89.4 nM when Compound I-7 was not present, 25.2 nM when Compound I-7 was present at a concentration of 2 µM, and 8.2 nM when Compound I-7 was present at a concentration of 4 µM. See FIG. 8.

Figure 9:
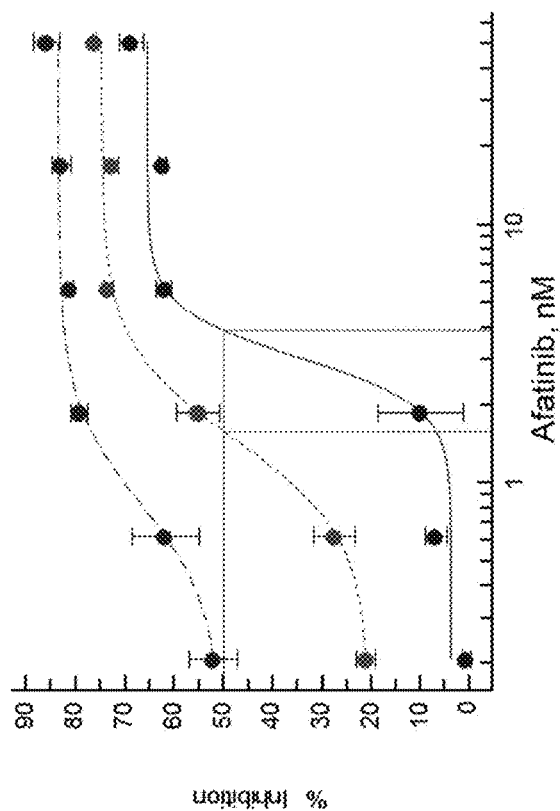
FIG. 9 shows the effect of combination of afatinib and Compound I-7 (0, 3, and 6 µM) on the growth of HCC827 cells.

HCC827 cells were cultured and treated as described in Examples 1 and 2. The highest concentration of afatinib used in this assay was 50 nM and the concentrations of Compound I-7 were 3 µM and 6 µM. The $EC_{50}$ values observed for afatinib were 3.8 nM when Compound I-7 was not present, 1.6 nM when Compound I-7 was present at a concentration of 3 µM, and 0.2 nM when Compound I-7 was present at a concentration of 6 µM. See FIG. 9.

Figure 10:
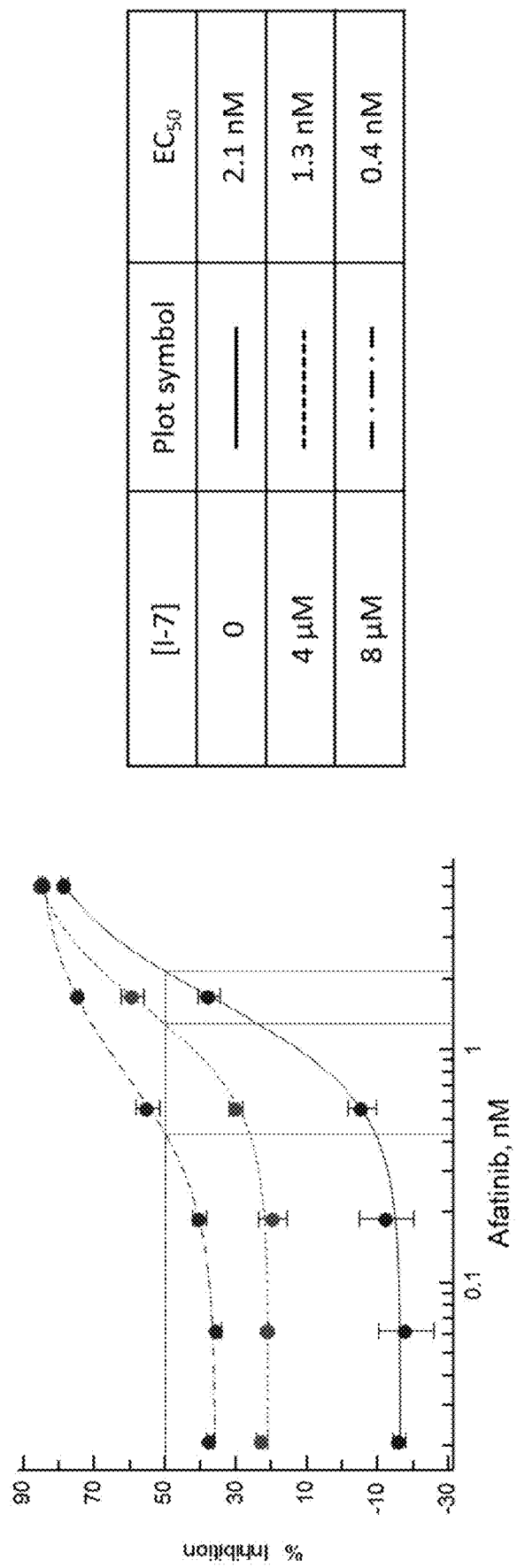
FIG. 10 shows the effect of combination of afatinib and Compound I-7 (0, 3, and 6 µM) on the growth of PC9 cells.

PC9 cells were cultured and treated as described in Examples 1 and 2. The highest concentration of afatinib used in this assay was 5 nM and the concentrations of Compound I-7 were 4 µM and 8 µM. The $EC_{50}$ values observed for afatinib were 2.1 nM when Compound I-7 was not present, 1.3 nM when Compound I-7 was present at a concentration of 3 µM, and 0.4 nM when Compound I-7 was present at a concentration of 6 µM. See FIG. 10.

Figure 11:
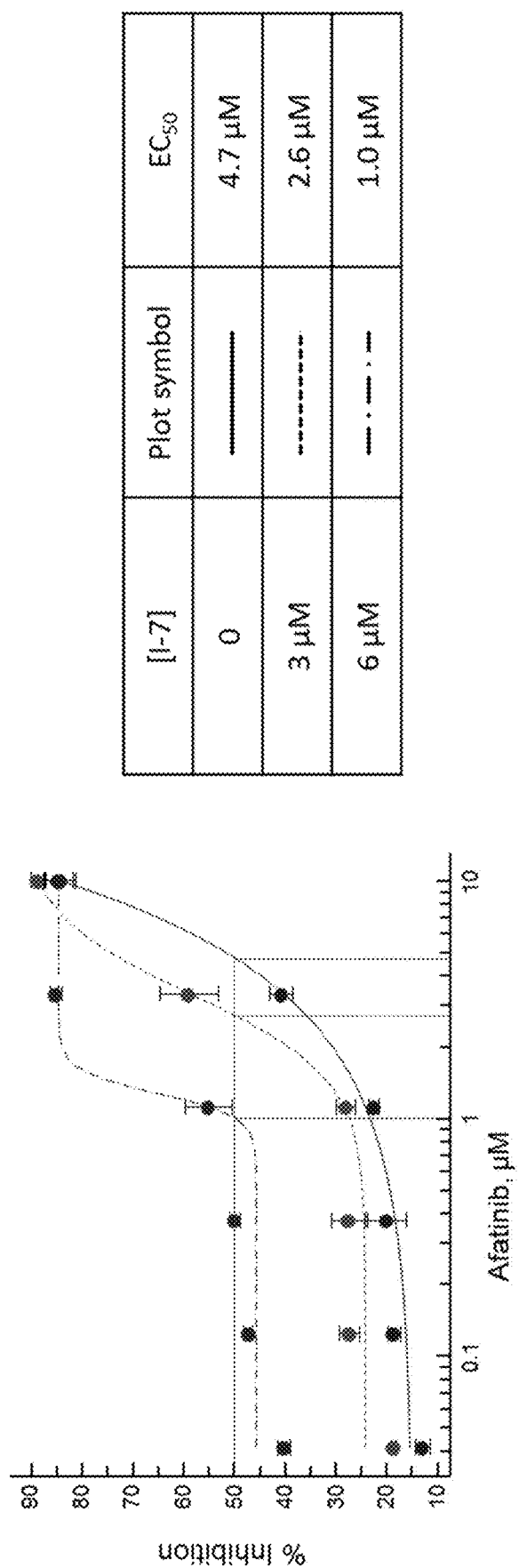
FIG. 11 shows the effect of combination of afatinib and Compound I-7 (0, 3, and 6 µM) on the growth of A549 cells.

A549 cells were cultured and treated as described in Examples 1 and 2. The highest concentration of afatinib used in this assay was 10 µM and the concentrations of Compound I-7 were 4 µM and 8 µM. The $EC_{50}$ values observed for afatinib were 4.7 µM when Compound I-7 was not present, 2.6 µM when Compound I-7 was present at a concentration of 3 µM, and 1.0 µM when Compound I-7 was present at a concentration of 6 µM. See FIG. 11.

Figure 12:
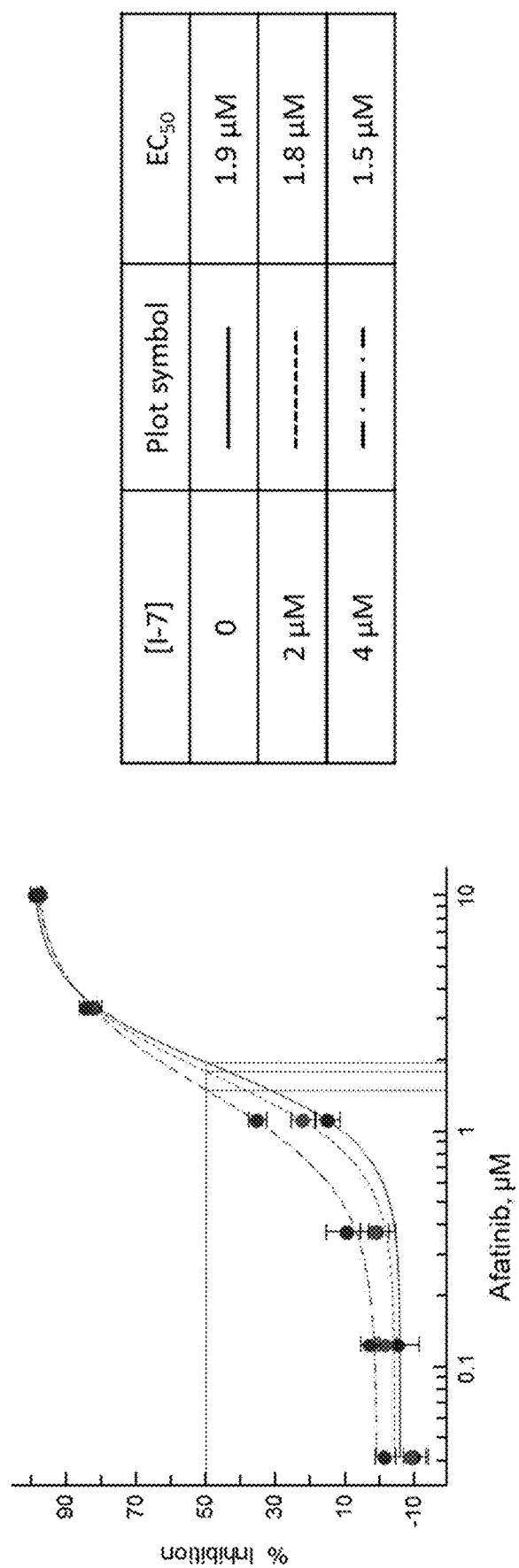
FIG. 12 shows the effect of combination of afatinib and Compound I-7 (0, 3, and 6 µM) on the growth of PANC1 cells.

PANC1 cells were cultured and treated as described in Examples 1 and 2. The highest concentration of afatinib used in this assay was 10 µM and the concentrations of Compound I-7 were 2 µM and 4 µM. The $EC_{50}$ values observed for afatinib were 1.9 µM when Compound I-7 was not present, 1.8 µM when Compound I-7 was present at a concentration of 2 µM, and 1.5 µM when Compound I-7 was present at a concentration of 4 µM. See FIG. 12.

In this experiment it was demonstrated that combining an irreversible EGFR inhibitor afatinib with Compound I-7 yielded a significant increase in cytotoxicity (lower $EC_{50}$ value) of afatinib against H1975 cells and other non-small cell lung cancer cells, HCC827, PC9, and A549. Further, it was demonstrated that combining afatinib with Compound I-7 yielded an increase in cytotoxicity against PANC1 pancreatic cancer cells. While this last combination may not be synergistic or result in a dramatic reduction in $EC_{50}$ values, it may well yield a significant improvement in the effectiveness of treatment relative to single therapy with an EGFR inhibitor by eradicating the resistant, quiescent cell populations in a neoplasm that otherwise survive the single therapy treatment.

Example 5

Figure 13:
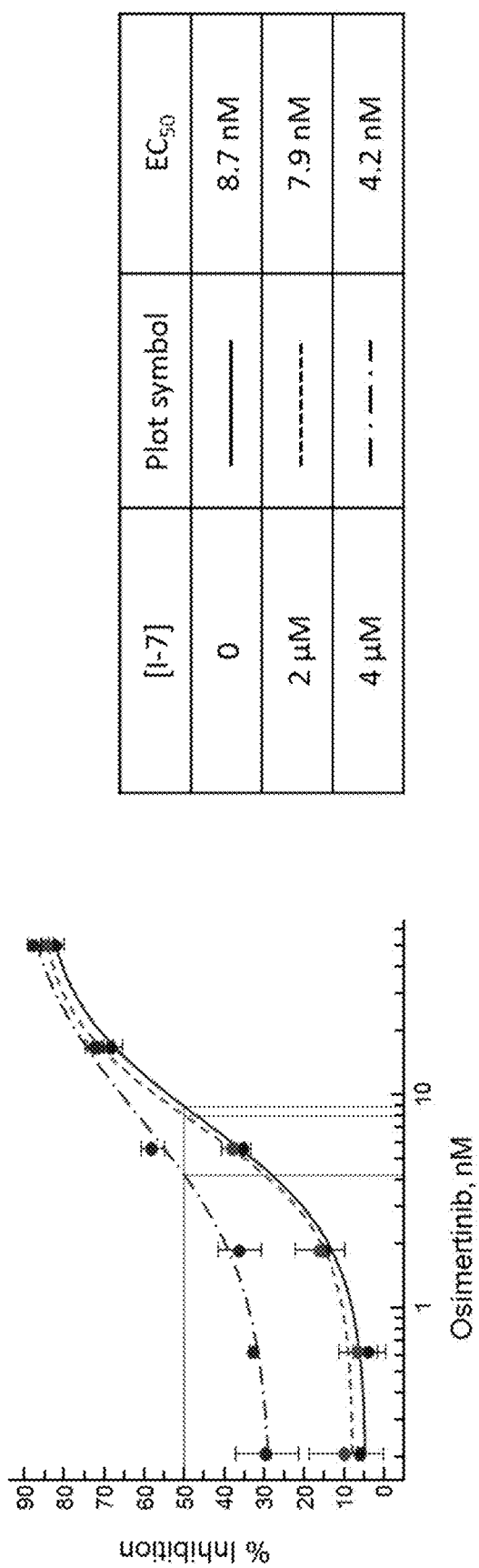
FIG. 13 shows the effect of combination of osimertinib and Compound I-7 (0, 2, and 4 µM) on the growth of H1975 cells.

Combination of a Molecule Effective Against Quiescent Cancer Cells With Osimertinib H1975 cells were cultured and treated as described in Examples 1 and 2. The highest concentration of osimertinib used in this assay was 50 nM and the concentrations of Compound I-7 were 2 µM and 4 µM. The $EC_{50}$ values observed were 8.7 nM when Compound I-7 was not present, 7.9 nM when Compound I-7 was present at a concentration of 2 µM, and 4.2 nM when Compound I-7 was present at a concentration of 4 µM. See FIG. 13.

Figure 14:
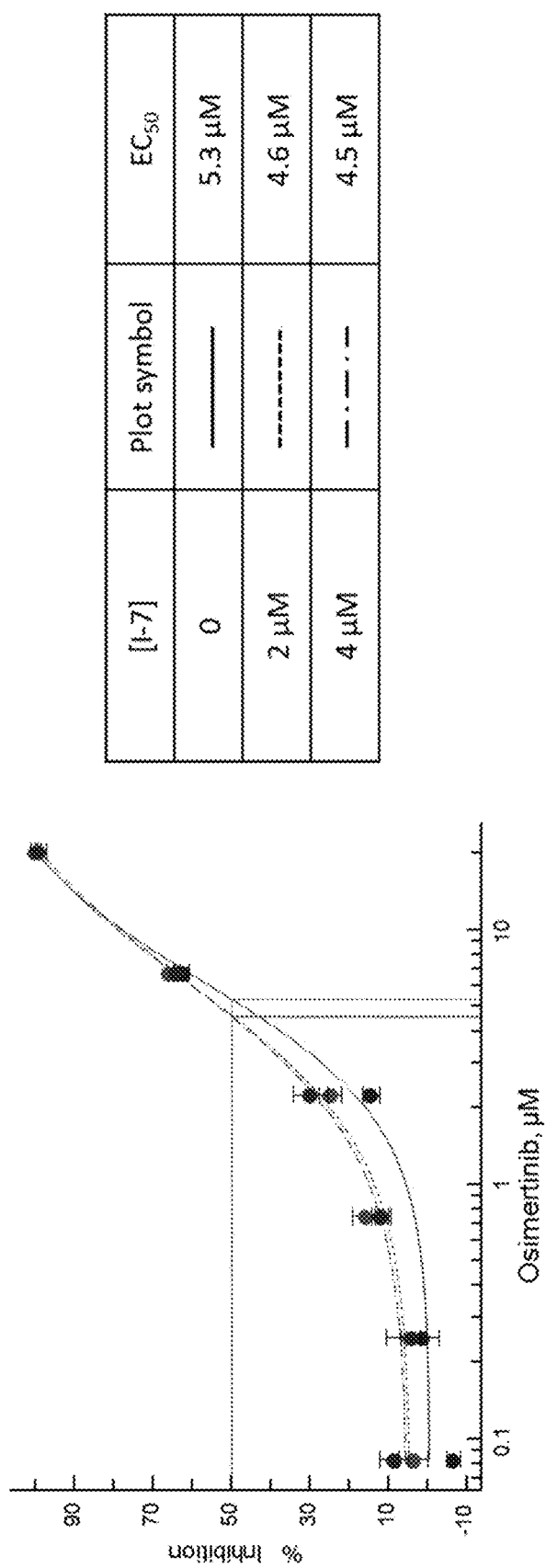
FIG. 14 shows the effect of combination of osimertinib and Compound I-7 (0, 2, and 4 µM) on the growth of PANC1 cells.

PANC1 cells were cultured and treated as described in Examples 1 and 2. The highest concentration of osimertinib used in this assay was 20 µM and the concentrations of Compound I-7 were 2 µM and 4 µM. The $EC_{50}$ values observed were 5.3 µM when Compound I-7 was not present, 4.6 µM when Compound I-7 was present at a concentration of 2 µM, and 4.5 µM when Compound I-7 was present at a concentration of 4 µM. See FIG. 14.

In this experiment it was demonstrated that combining an irreversible EGFR inhibitor osimertinib with Compound I-7 yielded a significant increase in cytotoxicity (lower $EC_{50}$ value) of osimertinib against H1975 cells. Further, it was demonstrated that combining osimertinib with Compound I-7 yielded an increase in cytotoxicity against PANC1 pancreatic cancer cells. While this last combination may not be synergistic or result in a dramatic reduction in $EC_{50}$ values, it may well yield a significant improvement in the effectiveness of treatment relative to single therapy with an EGFR inhibitor by eradicating the resistant, quiescent cell populations in a neoplasm that otherwise survive the single therapy treatment.

Example 6

Figure 15:
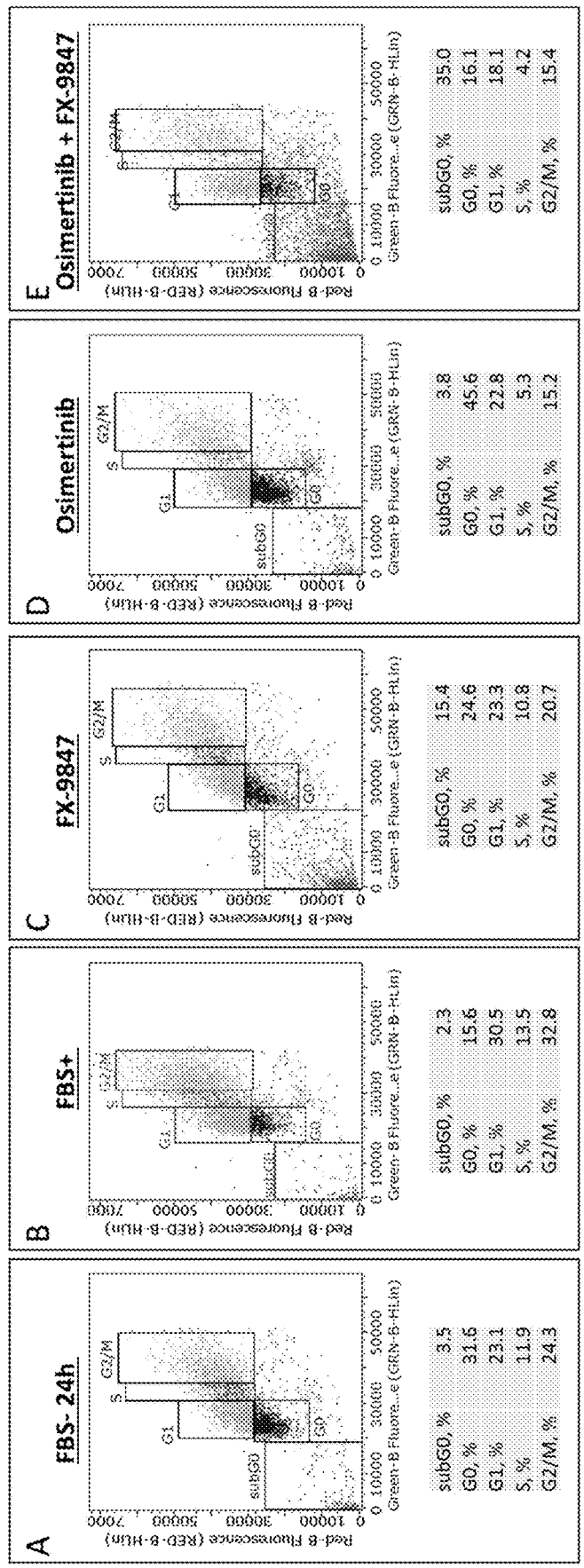
FIG. 15 shows FACS analyses of cell cycle distribution of H1975 cells incubated for 24 hours in Panel A: FBS− media; Panel B: FBS+ media; Panel C: FBS+ media with 5 µM Compound I-7; Panel D: FBS+ media with 18 nM osimertinib; Panel D: FBS+ media with 5 µM Compound I-7 and 18 nM osimertinib.
Figure 16:
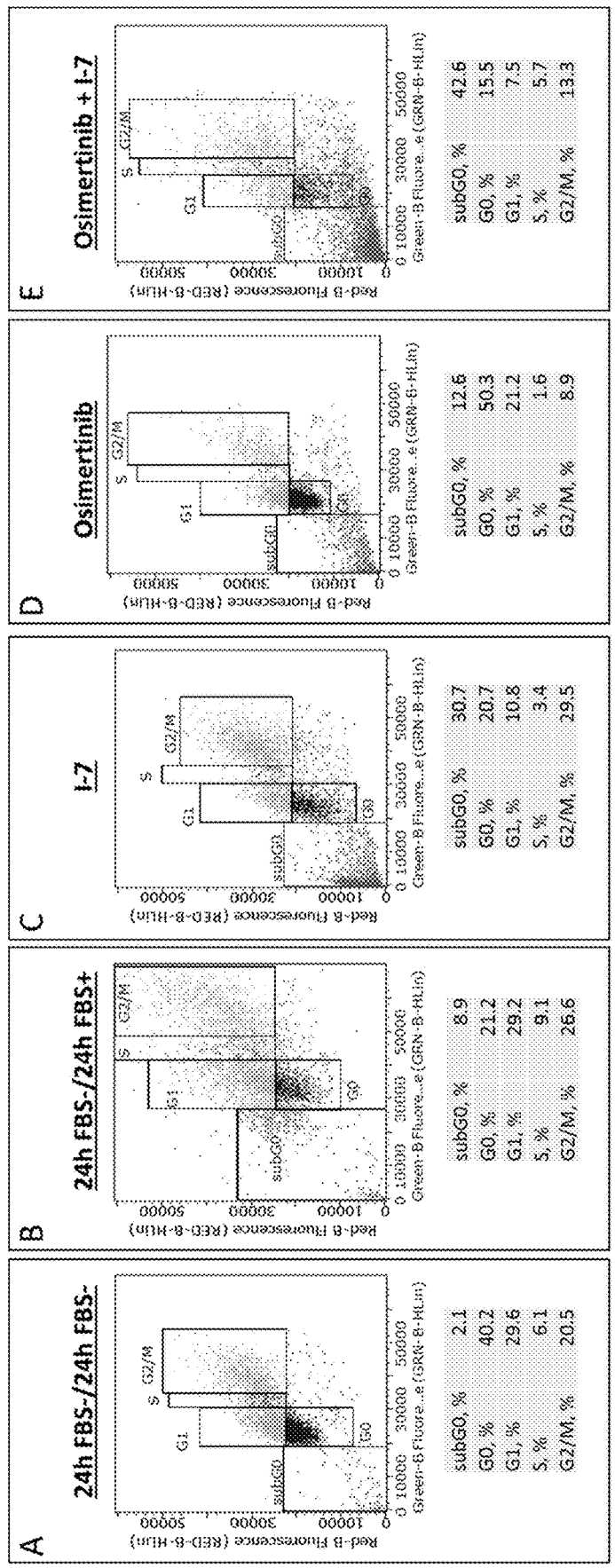
FIG. 16 shows FACS analyses of cell cycle distribution of H1975 cells incubated in Panel A: 48 hours FBS− media; Panel B: 24 hours in FBS− media followed by release in regular, FBS+ media for 24 hours; Panel C: 24 hours in FBS− media then release for 24 hours in FBS− media with 5 µM Compound I-7; Panel D: 24 hours in FBS− media then release for 24 hours in FBS− media with 18 nM osimertinib; Panel E: 24 hours in FBS− media then release for 24 hours in FBS− media with 18 nM osimertinib and 5 µM Compound I-7.

Cell Cycle Effects and Cytotoxicity of Osimertinib and Combination of a Molecule Effective Against Quiescent Cancer Cells With Osimertinib H1975 cells were cultured, treated, and analyzed as described in Examples 1 and 2. The results when different concentrations of osimertinib, Compound I-7, or both osimertinib and Compound I-7 are present are shown in FIGS. 15 & 16.

In these experiments it was demonstrated that exposure of H1975 cells to osimertinib results in changes in cell cycle distribution, such that osimertinib is even more effective than serum starvation (FBS−) at inducing a large fraction of the cells into the quiescent ($G_0$) state. The cell cycle distribution of normally proliferating H1975 cells, those incubated in serum free media (FBS−) and regular growth medium (FBS+), is shown for comparison. The osimertinib caused changes to the cell cycle distribution whether the cells were pre-incubated in normal growth medium (FBS+) or pre-starved in serum free (FBS−) medium to increase proportion of cells in $G_0$ prior to treatment with osimertinib. Further, combination of Compound I-7 with osimertinib reduced the fraction of cells in $G_0$ and strongly enhanced the resultant cytotoxicity as recorded by significant increases in apoptotic cells demonstrated as sub-$G_0$ population and demonstrated by viability assays. This effect was observed irrespective of whether or not the cells were pre-incubated in growth medium or under the conditions of serum starvation.

Example 7

Figure 17:
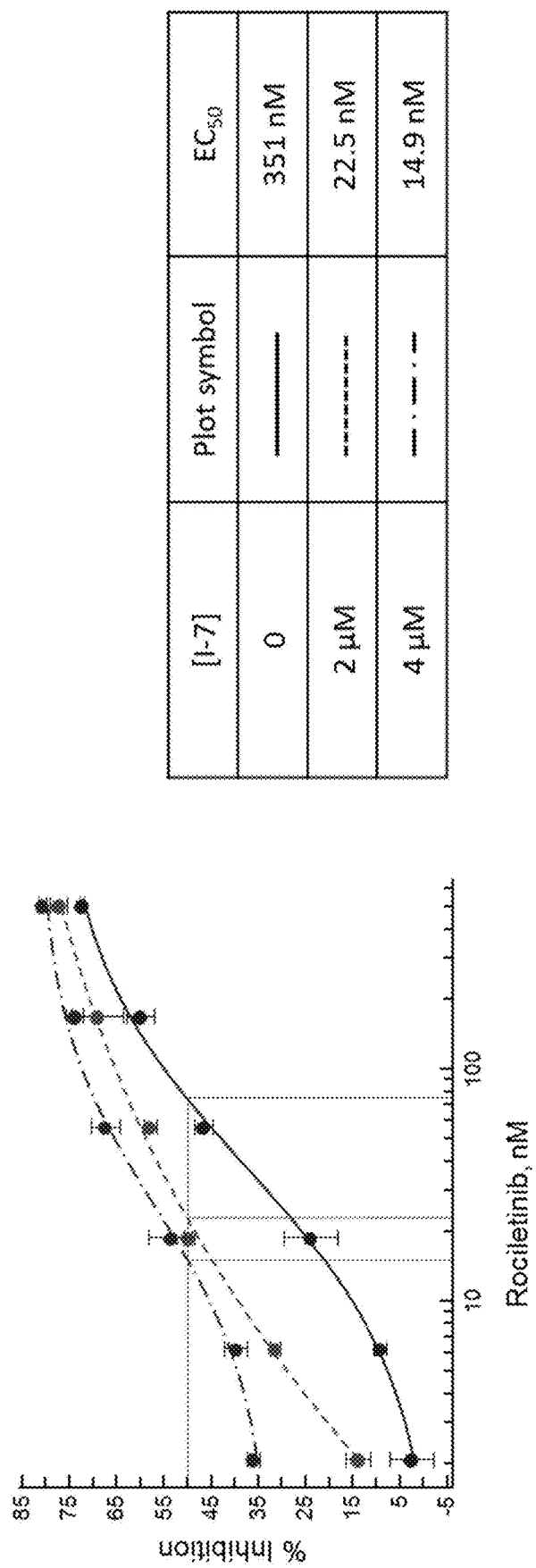
FIG. 17 shows effect of combination of rociletinib and Compound I-5 (0, 2.5, and 5 µM) on the growth of H1975 cells.

Combination of a Molecule Effective Against Quiescent Cancer Cells With Rociletinib The H1975 cells were cultured and treated as described in Examples 1 and 2. The highest concentration of rociletinib used in this assay was 500 nM and the concentrations of Compound I-7 were 2 µM and 4 µM. The $EC_{50}$ values observed for rociletinib inhibition were 351 nM when Compound I-7 was not present, 22.5 nM when Compound I-7 was present at a concentration of 2 and 14.9 nM when Compound I-7 was present at a concentration of 4 µM. See FIG. 17.

Figure 18:
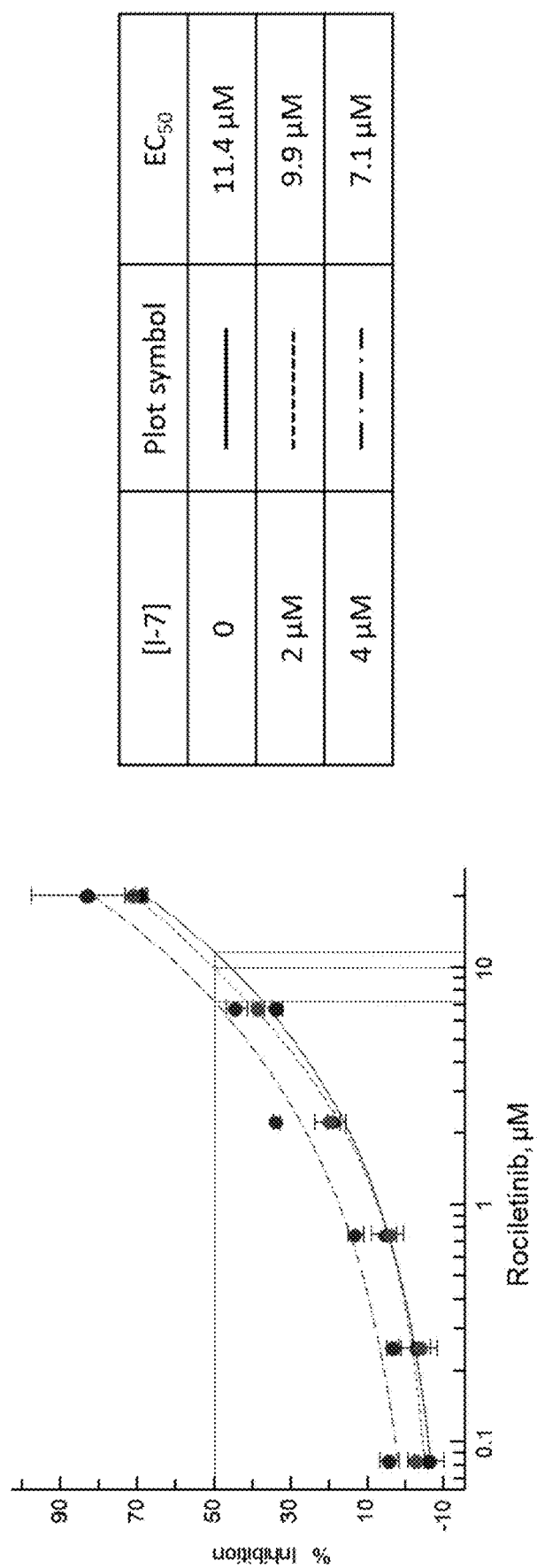
FIG. 18 shows effect of combination of rociletinib and Compound I-7 (0, 2, and 4 µM) on the growth of PANC1 cells.

PANC1 cells were cultured and treated as described in Examples 1 and 2. The highest concentration of rociletinib used in this assay was 20 µM and the concentrations of Compound I-7 were 2 µM and 4 µM. The $EC_{50}$ values observed were 11.4 µM when Compound I-7 was not present, 9.9 µM when Compound I-7 was present at a concentration of 2 and 7.1 µM when Compound I-7 was present at a concentration of 4 µM. See FIG. 18.

In this experiment it was demonstrated that combining an irreversible EGFR inhibitor rociletinib with Compound I-7 resulted in a significant increase in cytotoxicity (lower $EC_{50}$ value) of rociletinib against H1975 cells. Further, it was demonstrated that combining osimertinib with Compound I-7 yielded an increase in cytotoxicity (lower $EC_{50}$ value) against PANC1 pancreatic cancer cells. While this last combination may not be synergistic or result in a dramatic reduction in $EC_{50}$ values, it may well yield a significant improvement in the effectiveness of treatment relative to single therapy with an EGFR inhibitor by eradicating the resistant, quiescent cell populations in a neoplasm that otherwise survive the single therapy treatment.

Example 8

Figure 19:
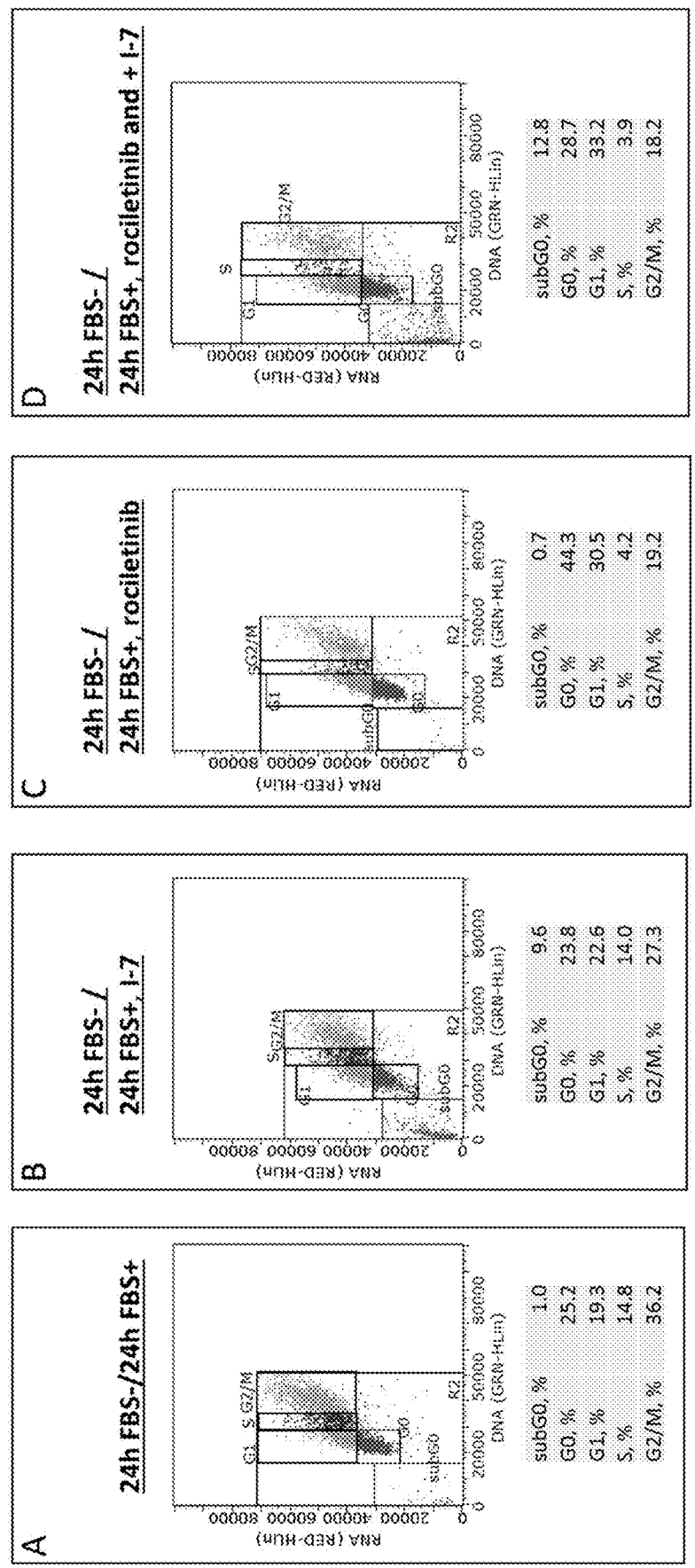
FIG. 19 shows FACS analyses of cell cycle distribution of H1975 cells incubated in Panel A: 24 hours in FBS− media then release for 24 hours in FBS+ media; Panel B: 24 hours in FBS− media then release for 24 hours in FBS+ media with 5 µM Compound I-7; Panel C: 24 hours in FBS− media then release for 24 hours in FBS+ media with 80 nM rociletinib; Panel D: 24 hours in FBS− media then release for 24 hours in FBS+ media with 80 nM rociletinib and 5 µM Compound I-7.

Cell Cycle Effects and Cytotoxicity of Rociletinib and Combination of a Molecule Effective Against Quiescent Cancer Cells With Rociletinib The H1975 cells were cultured, treated, and analyzed as described in Examples 1 and 2. The results when different concentrations of rociletinib, Compound I-7, or both rociletinib and Compound I-7 are present are shown in FIG. 19.

In this example, H1975 cells were incubated for 24 hours under the conditions of serum starvation (FBS−) and then "released" into normal growth medium (FBS+) with or without treatment. Under these conditions, exposure to rociletinib led to a significant increase in fraction of cells in quiescent state ($G_0$). When cells were co-treated with combination of rociletinib and Compound I-7 no such increase in proportion of quiescent cells was observed and a large increase in cytotoxicity of rociletinib was observed, as judged by the large increase in apoptotic cells as determined by sub-$G_0$ fraction.

Example 9

Induction of DYRK1B Upon Treatment of H1975 Cells With EGFR Inhibitors

H1975 cells were cultured and treated as described in Examples 1 and 2. For Western Blot analysis cells were seeded into 6-well plates at $5 \times 10^5$-$9 \times 10^5$ cells/well (depending on the cell size and rate of proliferation), allowed to attach for 24 hours, then treated with compounds for 24 hours, and harvested. Immunoblotting was performed using conventional techniques, as described in Cell Signaling Technologies Western Blotting protocol (www.cellsignal.com).

Antibodies used for blotting were from Cell Signaling Technology (CST): DYRK1B (D40D1) Rabbit mAb #5672; EGF Receptor (D38B1) XP® Rabbit mAb #4267; Phospho-EGF Receptor (Tyr1068) (D7A5) XP® Rabbit mAb #3777; β-Actin (13E5) Rabbit mAb #4970; Anti-rabbit IgG, HRP-linked Antibody #7074. The Primary Antibody Dilution Buffer 1X TBST with 5% BSA (CST #9998) was used. For detection, SignalFire™ ECL Reagent (CST #6883) was used.

Figure 20:
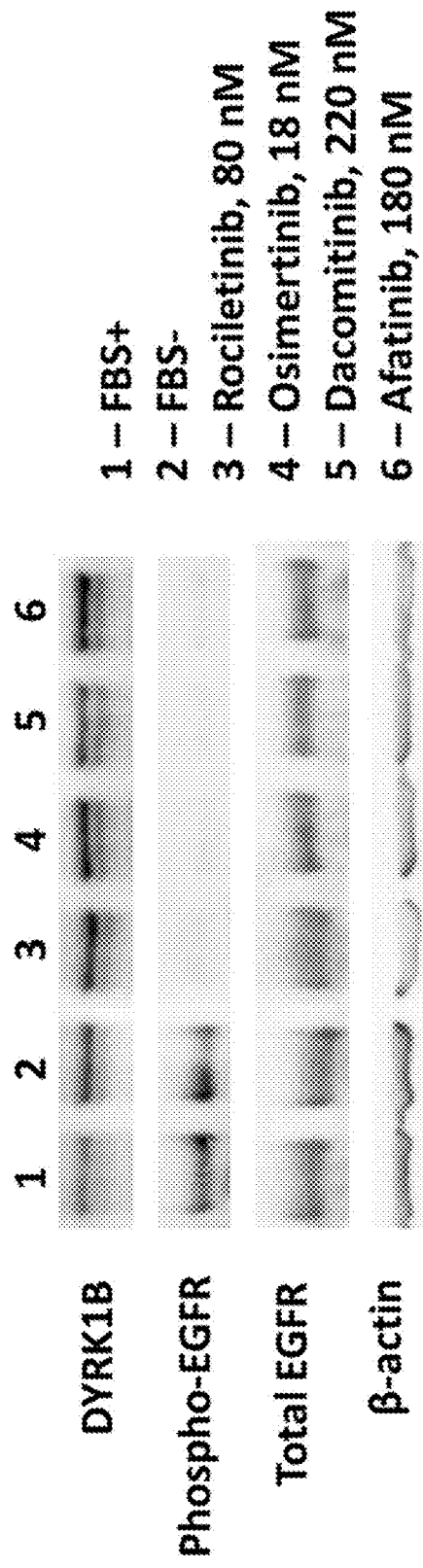
FIG. 20 shows Western blot analysis showing expression levels of DYRK1B, phosphorylated Y1068-EGFR, total EGFR, and β-actin in H1975 cells after 24 hour treatment with rociletinib, osimertinib, dacomitinib, and afatinib.

The expression levels of DYRK1B, ph-Y1068 EGFR, total EGFR, and β-actin in H1975 cells following the 24 hours treatment with rociletinib, osimertinib, dacomitinib, and afatinib as observed by Western blot analysis are shown in FIG. 20. The expression of DYRK1B protein was compared to that in untreated cells incubated in regular growth medium containing FBS (FBS+) or serum free medium (FBS−). It was demonstrated that treatment with each of the EGFR inhibitors suppressed the EGFR phosphorylation and also induced expression of DYRK1B protein similar to or higher than that produced by serum starvation.

Example 10

Figure 21:
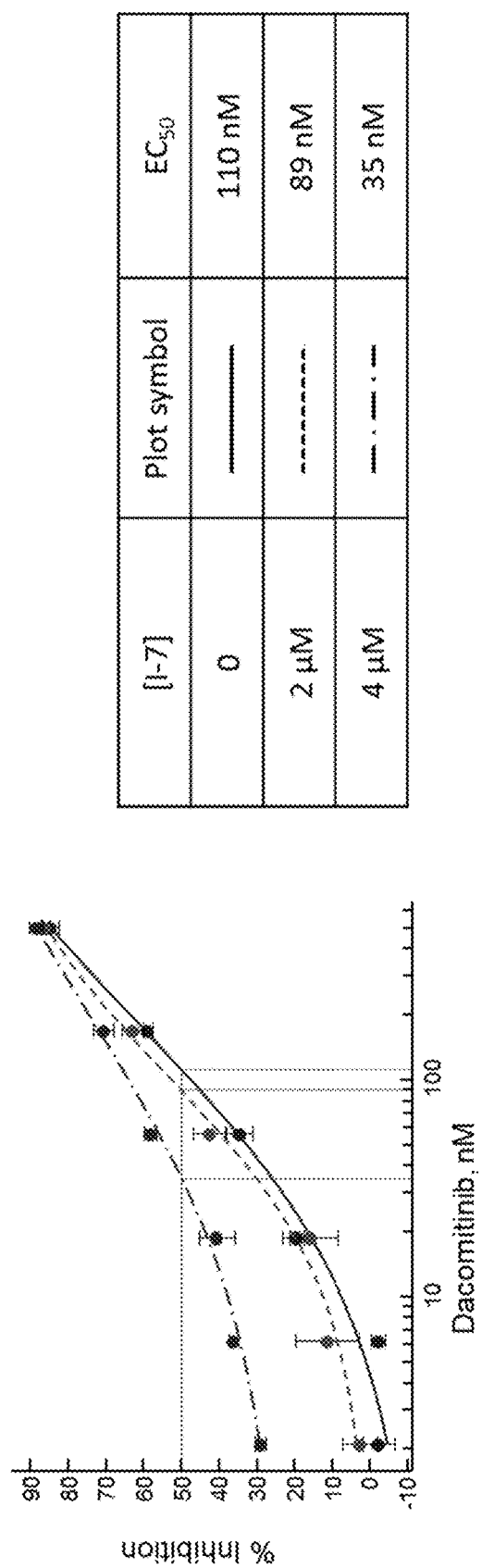
FIG. 21 shows effect of combination of dacomitinib and Compound I-5 (0, 2.5, and 5 µM) on the growth of H1975 cells.

Combination of a Molecule Effective Against Quiescent Cancer Cells With Dacomitinib The H1975 cells were cultured and treated as described in Examples 1 and 2. The highest concentration of dacomitinib used in this assay was 500 nM and the concentrations of Compound I-7 were 2 μM and 4 μM. The $EC_{50}$ values observed for dacomitinib inhibition were 110.3 nM when Compound I-7 was not present, 88.6 nM when Compound I-7 was present at a concentration of 2 μM, and 34.8 nM when Compound I-7 was present at a concentration of 4 μM. See FIG. 21.

Figure 22:
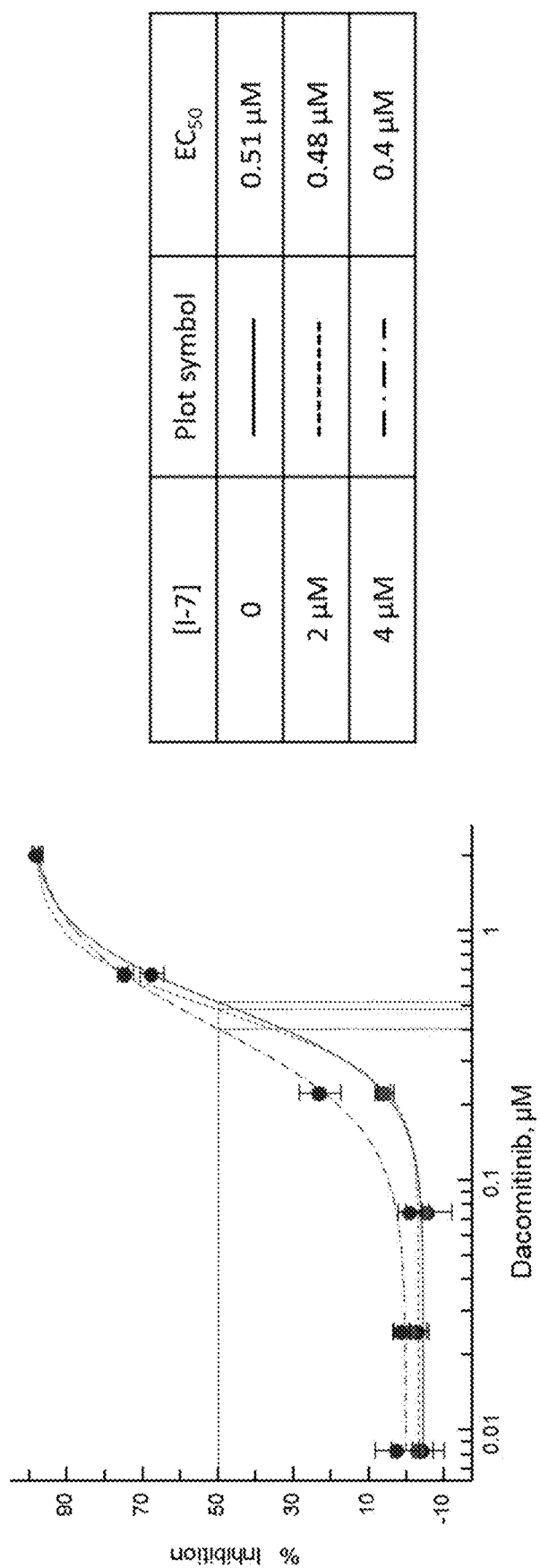
FIG. 22 shows effect of combination of dacomitinib and Compound I-7 (0, 2, and 4 µM) on the growth of PANC1 cells.

PANC1 cells were cultured and treated as described in Examples 1 and 2. The highest concentration of dacomitinib used in this assay was 10 μM and the concentrations of Compound I-7 were 2 μM and 4 μM. The $EC_{50}$ values observed were 11.4 μM when Compound I-7 was not present, 9.9 μM when Compound I-7 was present at a concentration of 2 μM, and 7.1 μM when Compound I-7 was present at a concentration of 4 μM. See FIG. 22.

In this experiment it was demonstrated that combining an irreversible EGFR inhibitor dacomitinib with Compound I-7 yielded a significant increase in cytotoxicity (lower $EC_{50}$ value) of dacomitinib against H1975 cells. Further, it was demonstrated that combining osimertinib with Compound I-7 yielded an increase in cytotoxicity against PANC1 pancreatic cancer cells. While this last combination may not be synergistic or result in a dramatic reduction in $EC_{50}$ values, it may well yield a significant improvement in the effectiveness of treatment relative to single therapy with an EGFR inhibitor by eradicating the resistant, quiescent cell populations in a neoplasm that otherwise survive the single therapy treatment.

Example 11

Cell Cycle Effects of AZ191 and Comparison With Compound I-7

The SW620 cells were cultured and treated as described in Example 1. For propidium iodide (PI) staining, manufacturer's protocol supplied with the Guava Cell Cycle Reagent for Flow Cytometry (EMD Millipore) was followed. The measurements were performed with Guava PCA-96 flow cytometer (EMD Millipore) using the green laser for excitation at 535 nm and monitoring emission at 617 nm.

Figure 23:
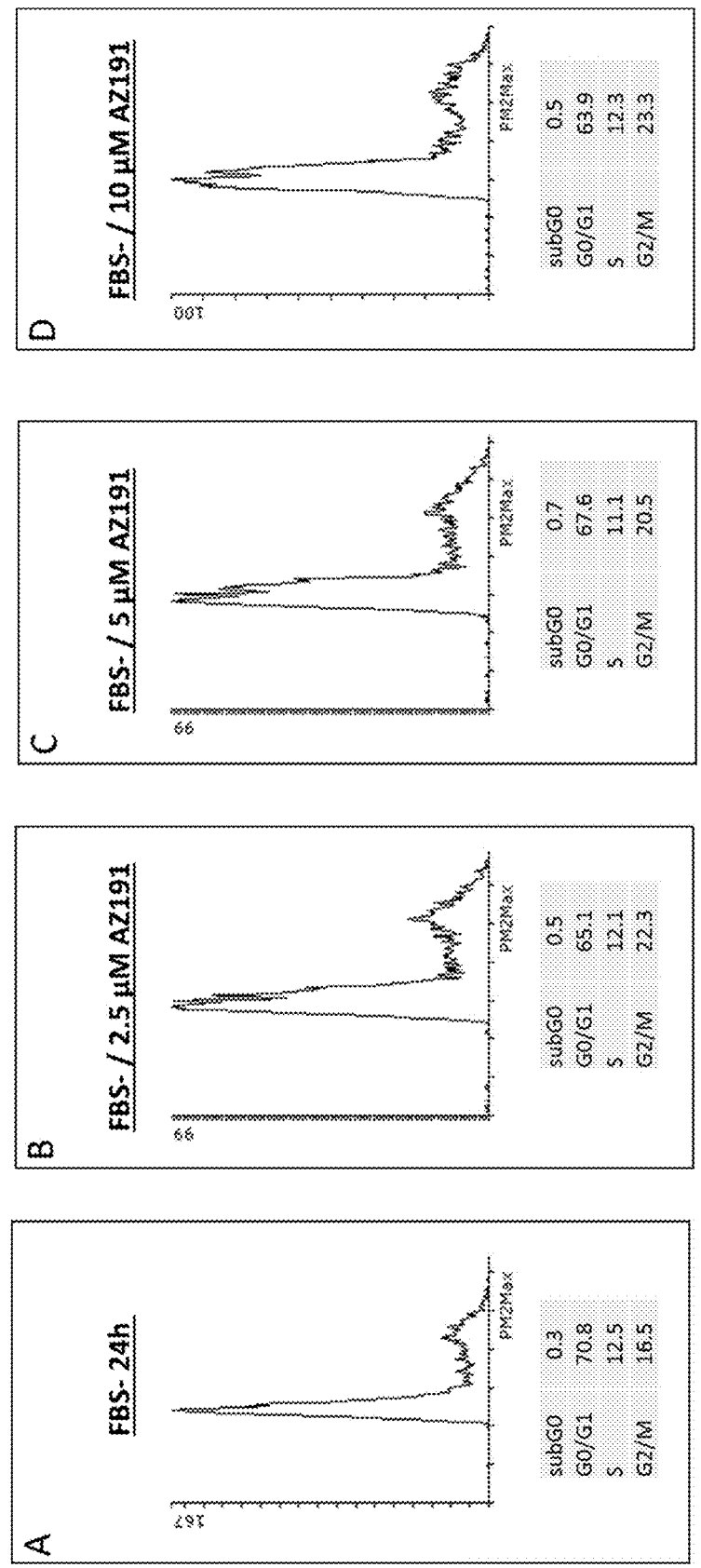
FIG. 23 shows FACS analyses by DNA content of cell cycle distribution of SW620 cells. The cells were incubated in Panel A: 24 hours in FBS− media; Panel B: 24 hours in FBS− media with 2.5 µM AZ191; Panel C: 24 hours in FBS− media with 5 µM AZ191; Panel D: 24 hours in FBS− media with 10 µM AZ191.

The results when different concentrations of AZ191 were present are shown in FIG. 23. The data are average of two replicates.

The SW620 cells were cultured, treated, and analyzed as described in Examples 1. For propidium iodide (PI) staining, manufacturer's protocol supplied with the Guava Cell Cycle Reagent for Flow Cytometry (EMD Millipore) was followed. The measurements were performed with Guava PCA-96 flow cytometer (EMD Millipore) using the green laser for excitation at 535 nm and monitoring emission at 617 nm.

Figure 24:
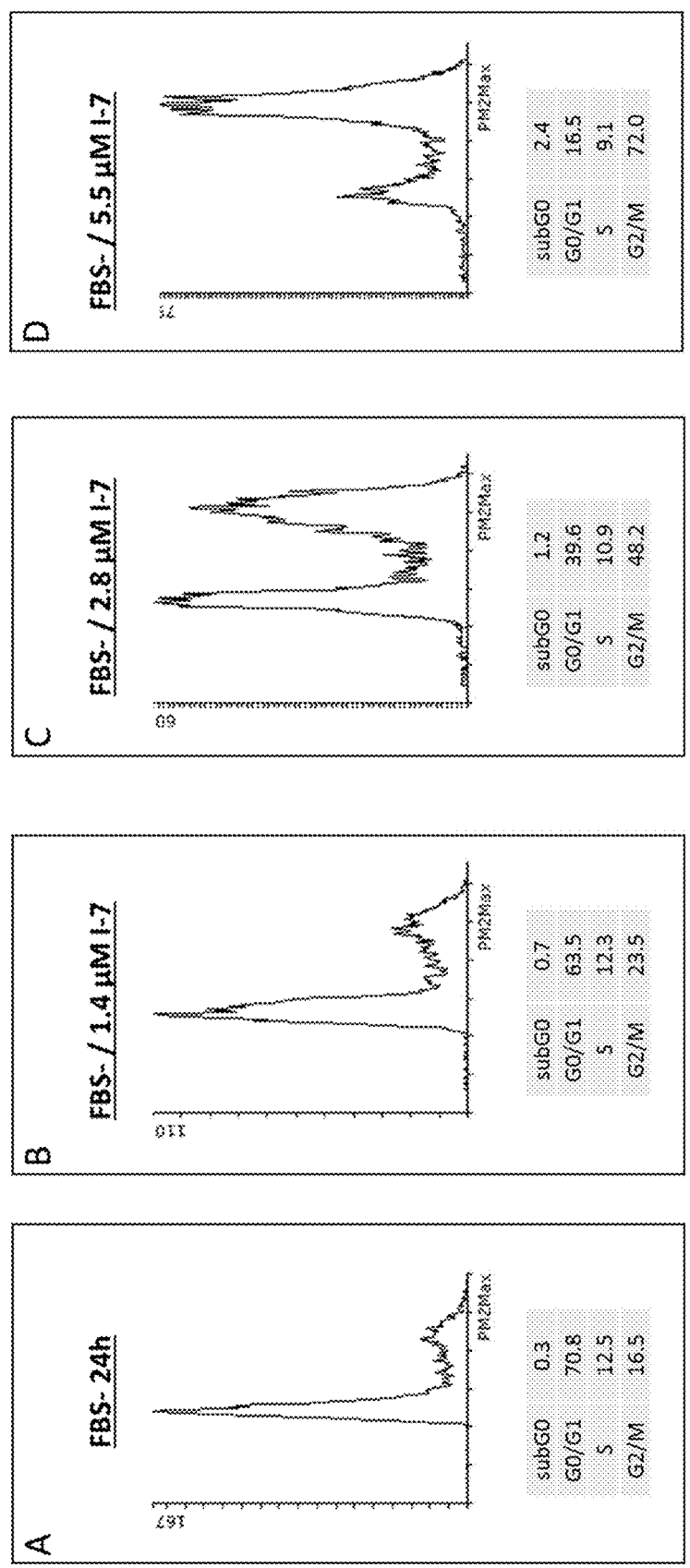
FIG. 24 shows FACS analyses by DNA content of cell cycle distribution of SW620 cells. The cells were incubated in Panel A: 24 hours in FBS− media with DMSO control; Panel B: 24 hours in FBS− media with 1.25 µM Compound I-7; Panel C: 24 hours in FBS-media 2.5 µM Compound I-7; Panel D: 24 hours in FBS− media with 5 µM Compound I-7.

The results when different concentrations of Compound I-7 were present are shown in FIG. 24. The data are average of two replicates.

In these experiments, SW620 cells were incubated for 24 hours in FBS− media, which contained different concentrations of either AZ191 or Compound I-7. Under these conditions, exposure to AZ191 led to no decrease in fraction of cells in quiescent state ($G_0$) based on no observed change in the fraction of cells $G_0+G_1$ phase. Under the same conditions, exposure to same or lower concentrations of Compound I-7 led to a significant decrease in fraction of cells in quiescent state ($G_0$) based on the significant decrease in the fraction of cells $G_0+G_1$ phase.

AZ191 inhibits DYRK1B at 17 nM (Ashford A L, Oxley D, Kettle J, Hudson K, Guichard S, Cook S J, Lochhead P A (2014) A novel DYRK1B inhibitor AZ191 demonstrates that DYRK1B acts independently of GSK3beta to phosphorylate cyclin D1 at Thr(286), not Thr(288). Biochemical Journal 457, 43-56).

In this experiment, it was demonstrated that not all DYRK1 inhibitors are effective against quiescent cancer cells.

Example 12

General Procedure for the Cell Viability Assays in 3D Cell Culture (Spheroids)

For viability analysis in 3D culture, cells were seeded into 96-well ULA (ultra-low attachment) plates (Corning #4515) at $5×10^3$-$6×10^3$ cells/well depending on cell size and rate of proliferation aiming for spheroid formation with diameter of 400-600 μM at the beginning of treatment. Cells were incubated for 2-3 days (depending on the cell line) at 37° C. in a humidified 5% $CO_2$ atmosphere allowing for tight spheroid formation. For the treatment, 50 μL of media was removed from each well and replaced with fresh media with compounds. The treatments were performed using at least 6 different concentrations of a compound in 1:3 serial dilutions. Before reading the results, cells were incubated for the period of 4-10 days in 5% $CO_2$ incubator at 37° C. If the treatment time exceeded 4 days, 70 of media in each well was replaced with fresh media containing the test compound every fourth day. Each treatment was performed in duplicate. Results were analyzed by CellTiter-Glo™ 3D Luminescent Cell Viability Assay (Promega, cat. # G9682) according to the manufacturer's instructions using SpectraMAX Gemini Spectrophotometer (Molecular Devices). Prior to analysis, the spheroids were photographed at 50× magnification.

Example 13

Figure 25:
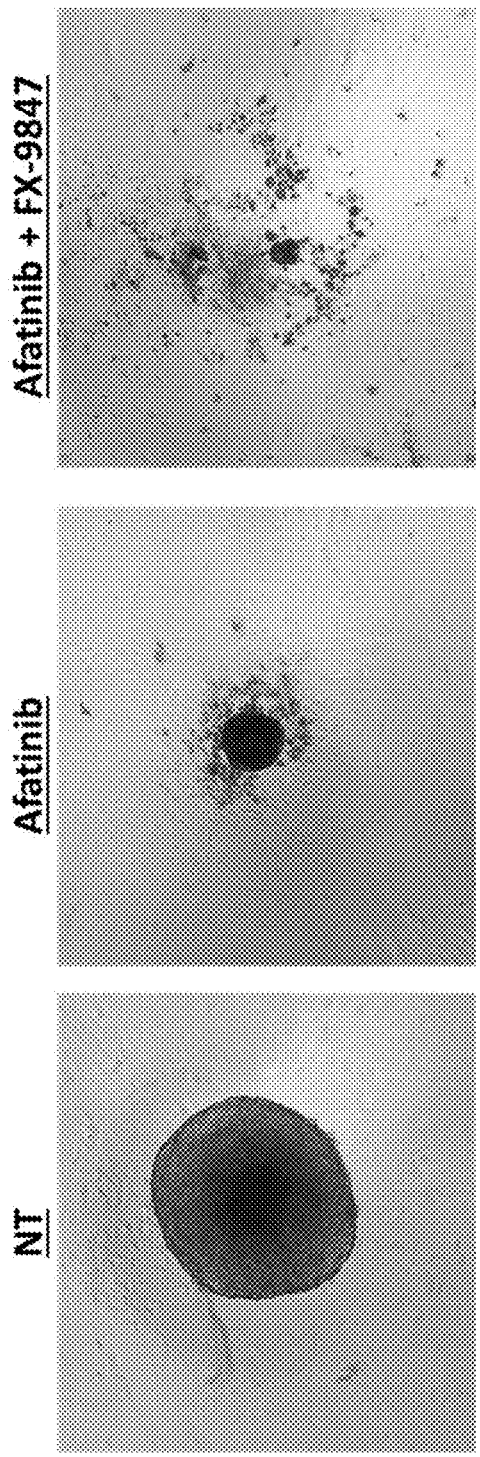
FIG. 25 shows the effect of combination of afatinib and Compound I-7 (0 ad 2.5 µM) on 3D cell culture (spheroids) of H1975 cells.

Combination of a Molecule Effective Against Quiescent Cancer Cells With Afatinib in 3D Cell Culture H1975 spheroids were cultured and treated as described in Examples 1 and 12. The concentration of afatinib used in this assay was 100 nM and the concentrations of Compound I-7 was 2.5 μM. The duration of treatment was seven days. See FIG. 25.

In this experiment it was demonstrated that combination therapy of an irreversible EGFR inhibitor afatinib with Compound I-7 resulted in a significant increase in cytotoxicity (lower $EC_{50}$ values) of afatinib against 3D culture (spheroid) of H1975 cells; the combination eradicated the spheroid completely whereas a portion of the spheroid survived treatment with afatinib alone.

Example 14

Figure 26:
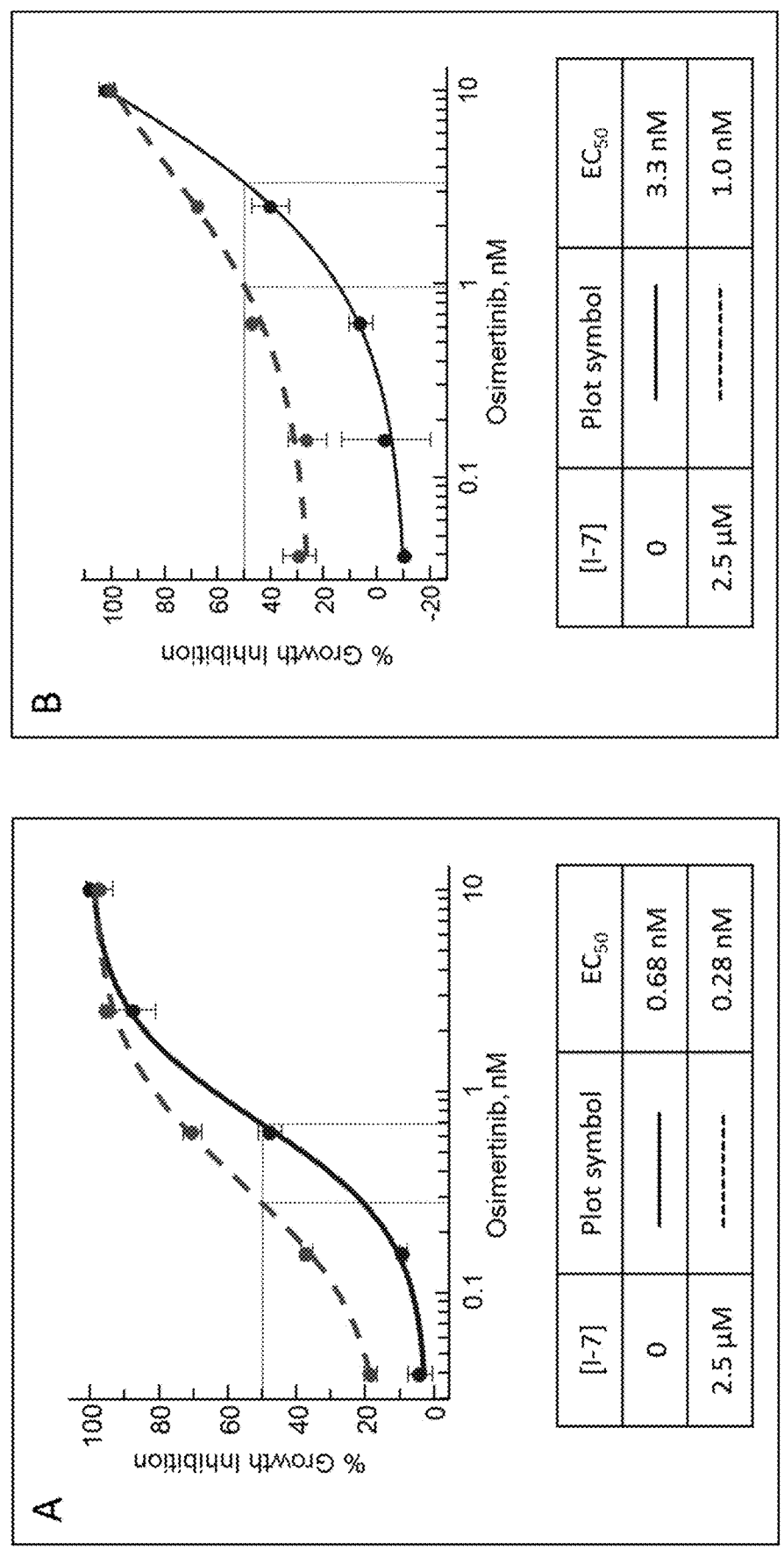
FIG. 26 shows the effect of combination of osimertinib and Compound I-7 (0 ad 2.5 µM) on 3D cell culture (spheroids) of H1975 cells. The spheroids were treated with different concentrations of osimertinib in Panel A: in FBS+ media; Panel B: in FBS− media.

Combination of a Molecule Effective Against Quiescent Cancer Cells With Osimertinib in 3D Cell Culture H1975 spheroids were cultured and treated for seven days as described in Examples 1, 2, and 12. The highest concentration of osimertinib used in this assay was 10 nM and the concentration of Compound I-7 was 2.5 μM. In regular growth media (FBS+), the $EC_{50}$ values determined for osimertinib were 0.68 nM when Compound I-7 was not present and 0.28 nM when Compound I-7 was present at a concentration of 2.5 μM. Under conditions of serum starvation (FBS−), the $EC_{50}$ values determined for osimertinib were 3.3 nM when Compound I-7 was not present and 1.0 nM when Compound I-7 was present at a concentration of 2.5 μM. See FIG. 26.

In this experiment it was demonstrated that combining an irreversible EGFR inhibitor osimertinib with Compound I-7 yielded a significant increase in cytotoxicity (decrease in $EC_{50}$) of osimertinib against 3D culture (spheroids) of H1975 cells, whether the spheroids were cultured in regular media (FBS+) or in depleted media (FBS−). Unexpectedly, the percent decrease in $EC_{50}$ was larger in FBS− than in FBS+3D cultures.

While this invention has been particularly shown and described with references to example embodiments thereof, it will be understood by those skilled in the art that various changes in form and details may be made therein without departing from the scope of the invention encompassed by the appended claims.

The invention claimed is:

1. A method for treating a subject having a neoplasm, the method comprising administering to the subject, sequentially or concomitantly,
   (a) a DYRK1 inhibitor which inhibits DYRK1A or DYRK1B kinase activity that reduces the fraction of quiescent cancer cells by at least 10% as determined by fraction of sub-$G_0$ phase cells in a FACS assay; and
   (b) an EGFR TKI,
wherein $EC_{50}$ of the EGFR TKI is reduced by at least 5-fold or more in cell-based assays in the presence of the DYRK1 inhibitor as compared to the absence of the DYRK1 inhibitor;
therby treating the subject having the neoplasm.

2. The method of claim 1, wherein the neoplasm being treated is a primary or a metastatic cancer selected from biliary cancer, brain cancer, breast cancer, cervical cancer, colon cancer, gastric cancer, kidney cancer, head and neck cancer, leukemia, liver cancer, lung cancer, lymphoma, ovarian cancer, prostate cancer, rectal cancer, sarcoma, skin cancer, testicular cancer, thyroid cancer, uterine cancer, bladder cancer, breast cancer, colorectal cancer, small cell lung cancer, ovarian cancer, and prostate cancer.

3. The method of claim 1, wherein the neoplasm being treated is either a primary or metastatic non-small cell lung cancer.

4. The method of claim 1, wherein the neoplasm being treated is either a primary or metastatic pancreatic cancer.

5. The method of claim 1, wherein the EGFR TKI is a reversible inhibitor, selected from a list of brigatinib, CUDC-101, erlotinib, gefitinib, icotinib, lapatinib, sapitinib, tesevatinib, Tyrphostin AG 1478, vandetanib, and varlitinib.

6. The method of claim 1, wherein the EGFR TKI is EGFR TKI is selected from AZD3759 and MTKi-327 (JNJ-26483327).

7. The method of claim 1, wherein the EGFR TKI is an irreversible inhibitor, selected from a list of afatinib, canertinib, CL-387785 (EKI-785), CNX-2006, dacomitinib, naquotinib (ASP8273), neratinib, olmutinib (HM61713), osimertinib, PD168393, pelitinib, poziotinib, TAK285, rociletinib, and WZ4002.

8. The method of claim 1, wherein the EGFR TKI is selected from a list of allitinib (ALS-1306; AST-1306), AV-412 (MP-412), nazartinib (EGF816), and pyrotinib.

9. The method of claim 1, wherein the DYRK1 inhibitor is selected from I-1, I-2, I-3, I-4, I-5, I-6, and I-7.

* * * * *